United States Patent
McNair

(10) Patent No.: US 12,057,228 B1
(45) Date of Patent: Aug. 6, 2024

(54) PREDICTING NEWLY INCIDENT CHRONIC KIDNEY DISEASE

(71) Applicant: CERNER INNOVATION, INC., Kansas City, KS (US)

(72) Inventor: Douglas S. McNair, Leawood, KS (US)

(73) Assignee: Cerner Innovation, Inc., Kansas City, MO (US)

( * ) Notice: Subject to any disclaimer, the term of this patent is extended or adjusted under 35 U.S.C. 154(b) by 1126 days.

(21) Appl. No.: 15/392,040

(22) Filed: Dec. 28, 2016

Related U.S. Application Data

(60) Provisional application No. 62/272,677, filed on Dec. 30, 2015.

(51) Int. Cl.
| | |
|---|---|
| *G16H 50/20* | (2018.01) |
| *G06Q 10/1093* | (2023.01) |
| *G16H 10/60* | (2018.01) |
| *G16H 20/30* | (2018.01) |
| *G16H 50/30* | (2018.01) |
| *G16H 50/50* | (2018.01) |

(52) U.S. Cl.
CPC ......... *G16H 50/20* (2018.01); *G06Q 10/1095* (2013.01); *G16H 20/30* (2018.01); *G16H 50/30* (2018.01); *G16H 50/50* (2018.01); *G16H 10/60* (2018.01)

(58) Field of Classification Search
CPC .......... G06Q 50/22–24; G06Q 10/1095; G06F 17/11; G06F 19/3481; G06N 5/04
See application file for complete search history.

(56) References Cited

U.S. PATENT DOCUMENTS

| | | | | |
|---|---|---|---|---|
| 277,546 | A | * 5/1883 | Soykan et al. | ..... B61D 27/0036 237/35 |
| 8,208,984 | B2 | * 6/2012 | Blomquist | ........ A61M 5/14244 600/347 |

(Continued)

OTHER PUBLICATIONS

Toyama et al., "Relationship between Serum Uric Acid Levels and Chronic Kidney Disease in a Japanese Cohort with Normal or Mildly Reduced Kidney Function", Published online Sep. 10, 2015, PLOS One 2015 10(9). (Year: 2015).*

(Continued)

*Primary Examiner* — Evangeline Barr
*Assistant Examiner* — Anne-Marie K Alderson
(74) *Attorney, Agent, or Firm* — Mughal Gaudry & Franklin PC

(57) ABSTRACT

Systems, methods and computer-readable media are provided for identifying patients having an elevated near-term risk of chronic kidney disease (CKD) progression, including predicting an individual's risk of progression to Stage 3 CKD within a future time interval, which may be up to 36 months. Based on the prediction, appropriate care providers may be notified so that the risk of CKD progression may be mitigated. In an embodiment, measurements of physiological variables are obtained, including serial measurements for uric acid levels from a longitudinal time series of serum or plasma samples spanning the previous two to five years. An annualized uric acid velocity of the patient is determined and used to generate a multivariable mathematical model for determining a likelihood of risk for developing Stage 3 CKD within 36 months.

20 Claims, 13 Drawing Sheets

(56) References Cited

U.S. PATENT DOCUMENTS

| | | | | |
|---|---|---|---|---|
| 9,115,072 | B2* | 8/2015 | O'Neil | A61K 31/192 |
| 2007/0027636 | A1* | 2/2007 | Rabinowitz | G16H 50/50 |
| | | | | 702/20 |
| 2009/0062624 | A1* | 3/2009 | Neville | G16H 50/20 |
| | | | | 600/300 |
| 2009/0204439 | A1* | 8/2009 | Turton | G06Q 30/0217 |
| | | | | 705/3 |
| 2011/0143381 | A1* | 6/2011 | Barasch | G01N 33/6893 |
| | | | | 435/7.92 |
| 2011/0166883 | A1* | 7/2011 | Palmer | G16H 40/20 |
| | | | | 705/3 |
| 2011/0245283 | A1* | 10/2011 | Murata | G16H 50/80 |
| | | | | 514/275 |
| 2012/0107420 | A1* | 5/2012 | Breit | G01N 33/6893 |
| | | | | 424/682 |
| 2012/0277546 | A1* | 11/2012 | Soykan | A61M 1/14 |
| | | | | 600/301 |
| 2014/0095201 | A1* | 4/2014 | Farooq | G16H 50/30 |
| | | | | 705/3 |
| 2016/0116486 | A1* | 4/2016 | Perichon | G01N 33/5308 |
| | | | | 506/9 |
| 2017/0115310 | A1* | 4/2017 | Colhoun | G01N 33/50 |
| 2020/0096523 | A1* | 3/2020 | Broueilh | G01N 33/6863 |

OTHER PUBLICATIONS

Nick, T.G., Campbell, K.M. (2007). Logistic Regression. in: Ambrosius, W.T. (eds) Topics in Biostatistics. Methods in Molecular Biology™, vol. 404. Humana Press. https://doi.org/10.1007/978-1-59745-530-5_14 (Year: 2007).*

Weiner, D.E. et al., Uric Acid and Incident Kidney Disease in the Community, J Am Soc Nephrol 19: 1204-1211. (Year: 2008).*

Chonchol et. al., "Relationship of Uric Acid With Progression of Kidney Disease", American Journal of Kidney Diseases, vol. 50, No. 2 (Aug. 2007): pp. 239-247 (Year: 2007).*

Bellomo et. al. ",Association of Uric Acid With Change in Kidney Function in Healthy Normotensive Individuals", Am J Kidney Dis 56 :264-272. (Year: 2010).*

* cited by examiner

| CKD | eGFR (mL/min/m²) |
|---|---|
| Stage 1 | ≥ 90 |
| Stage 2 | 60 - 89 |
| Stage 3A | 45 - 59 |
| Stage 3B | 30 - 44 |
| Stage 4 | 15 - 29 |
| Stage 5 | < 15 |

Stage 1, Stage 2, Stage 3A: Mild symptoms
Stage 3B, Stage 4: ↑ Symptoms, ↑ Spend
Stage 5: End-stage / dialysis / KTx

FEMALE

| Patient... | enter |
|---|---|
| • Age (yr) | 35 |
| • eGFR (mL/min/1.73m$^2$) | 66 |
| • HbA1c (%) | 7.2 |
| • Uric Acid (mg/dL) | 5.7 |
| • Uric Acid Velocity (mg/dL/yr) | 0.23 |
| evaluate | results |
| data complete? | Yes |
| Probability of eGFR < 60 within 36 months | 37% |

MALE

| Patient... | enter |
|---|---|
| • Age (yr) | 35 |
| • eGFR (mL/min/1.73m$^2$) | 66 |
| • HbA1c (%) | 7.2 |
| • Uric Acid (mg/dL) | 5.7 |
| • Uric Acid Velocity (mg/dL/yr) | 0.23 |
| evaluate | results |
| data complete? | Yes |
| Probability of eGFR < 60 within 36 months | 97% |

FIG. 5B

| ITEM | VALUE |
|---|---|
| SENSITIVITY | 84% |
| SPECIFICITY | 91% |
| EVENT PREVALENCE | 29% |
| POSITIVE PREDICTIVE VALUE (PPV) | 79% |
| NEGATIVE PREDICTIVE VALUE (NPV) | 93% |

```
##################################################################

# pre-CKD predictor forecast probability of eGFR < 60 within 36 months

############################################################ library(DistributionUtils)
library(pROC)

# load pre-CKD and outcomes data
p_m <- read.csv(file="c:/0_cerdsm/IP/nephrology_CKD_preCKD_prediction/dsm_preCKD_male.csv", header=TRUE, colClasses=c("character","integer","numeric",rep("integer",2),rep("numeric",7),"integer",rep("character",4),rep("numeric",7),rep("integer",2)))
p_f <- read.csv(file="c:/0_cerdsm/IP/nephrology_CKD_preCKD_prediction/
dsm_preCKD_female.csv", header=TRUE, colClasses=c("character","integer","numeric",rep("integer",2),rep("numeric",7),"integer",rep("character",4),rep("numeric",7),rep("integer",2)))

pat,age,agexf,age_dec,gender,creat,egfr,egfrxf,uric1,uric2,uric3,uric4,uric4q,date1,date2,date3,
date4,t11,t12,t13,t14,uric_vel,hba1c,hba1cxf,hba1cgt85,ckd36 agexf      <- EXP(=6.120 + 0.102*C2)/(1 + EXP(-6.120 + 0.102*C2))
egfrxf     <- (100 - MAX(60,MIN(100,C3)))/40
# hba1cgt85  <- IF(C4>8.5,1,0)
# hba1cxf    <- EXP(-12.92 + 1.623*C7)/(1 + EXP(-12.92 + 1.623*C7))
# uric4q     <- IF(C5>VLOOKUP(age_decade,4q_table,75th_pctile),1,0)
# uric_vel   <- MAX(0,C6) ; in mg/dL/yr at least 4 serum uric acid measurements within past 3 years
# 4q_table mg/dL
# age decade  75th pctile female  75th pctile male
# 1           4.4                 4.5
# 2           5.2                 6.4
# 3           5.2                 6.7
# 4           5.2                 7.1
# 5           5.3                 7.1
# 6           5.8                 7.1
# 7           6.2                 7.0
# 8           6.4                 6.9
9           6.5                 6.8 calculate logistic regression models
fit_f <- glm(ckd36 ~ agexf + egfrxf + hba1cxf + uric4q + uric_vel, data=p_f, family=binomial())
summary(fit_f)
#             Estimate  Std. Error  z value  Pr(>|z|)
# (Intercept) -8.608    1.557       -5.530   3.2e-08  ***
# agexf        4.782    1.628        2.938   0.00331  **
# egfrxf       2.980    1.824        1.634   0.04229  *
# hba1cxf      6.954    3.016        2.306   0.02113  *
# uric4q       0.768    0.532        1.445   0.04852  *
# uric_vel    12.365    2.248        5.500   3.8e-08  ***
```

⋮

CONTINUES IN FIG. 7B

FIG. 7A

CONTINUES FROM FIG. 7A

. . .

```
fit_m <- glm(ckd36 ~ egfrxf + hba1cxf + uric_vel, data=p_m, family=binomial())
summary(fit_m)
#             Estimate  Std. Error  z value  Pr(>|z|)
# (Intercept) -8.482    1.412       -6.007   1.89e-09  ***
# egfrxf      10.192    1.939        5.255   1.48e-07  ***
# hba1cxf     3.884     2.111        1.840   0.0658    .
uric_vel    10.948    1.907        5.742   9.34e-09  *** evaluate model ROC curve
ds4 <- read.csv(file="c:/0_cerdsm/IP/nephrology_CKD_preCKD_prediction/roc.csv")
roc1 <- roc(ds4[,1] ~ ds4[,2], percent=TRUE,
# arguments for auc
# partial.auc=c(100,90), partial.auc.correct=TRUE,
# partial.auc.focus="sens",
# arguments for ci
  ci=TRUE, boot.n=100, ci.alpha=0.9, stratified=FALSE,
# arguments for plot
# auc.polygon=TRUE, max.auc.polygon=TRUE,
  plot=TRUE, grid=TRUE, print.auc=TRUE, show.thres=TRUE)
sens.ci <- ci.se(roc1, specificities=seq(0,100,5))
plot(sens.ci, type="shape", col="lightblue")
plot(sens.ci, type="bars")
# AUC = 86.2% (82.1-90.3)

#calculate significance (column-major)
table(ds4[,1], ds4[,2])
#    0    1
# 0  231  17
1  23   88 x2 <- matrix(c(88,17,23,231), nrow=2)
fisher.test(x2, alternative="two.sided")

# sensitivity = 84% (80-88)
# specificity = 91% (88-94)
# prevalence = 29% (25-34)
# PPV = 79% (75-83)
# NPV = 93% (91-96)
# OR = 50.9
# Fisher chi-sq p-value = 2.2e-16
```

FIG. 7B

PREDICTING NEWLY INCIDENT CHRONIC KIDNEY DISEASE

CROSS-REFERENCE TO RELATED APPLICATIONS

This application claims the benefit of U.S. Provisional Application No. 62/272,677 titled "PREDICTING NEWLY INCIDENT CHRONIC KIDNEY DISEASE," filed on Dec. 30, 2015; which is hereby expressly incorporated by reference in its entirety.

BACKGROUND

Chronic kidney disease (CKD) is increasing in epidemiologic and economic importance in developed nations. Chronic kidney disease globally resulted in 735,000 deaths in 2010, a substantial increase from 400,000 deaths in 1990. In the United States, the Centers for Disease Control and Prevention found that CKD affected an estimated 16.8% of adults aged 20 years and older, during 1999 to 2004, and estimates from the National Health Service for the United Kingdom suggest that 8.8% of the population of Great Britain and Northern Ireland have symptomatic CKD. Presently 26 million American adults have CKD. Total Medicare expenditures for CKD in 2011 exceeded $45 billion. Additionally, diagnoses of cardiovascular-related comorbidities (hypertension, hypercholesterolemia, diabetes and cardiovascular disease) increase with worsening CKD severity. Annual health spending increases with increasing severity and comorbidities, and quality of life diminishes.

SUMMARY

Systems, methods and computer-readable media are provided for identification of patients having an elevated near-term risk of chronic kidney disease progression. Embodiments of this disclosure are directed to event prediction, risk stratification, and optimization of the assessment, communication, and decision-making to prevent, treat, and or manage chronic kidney disease events in humans, and in one embodiment take the form of a platform for embedded decision support in an electronic health record (EHR) system. In particular, embodiments of the invention facilitate monitoring human patients and quantitatively predicting whether or not an elevated risk of progression of Stage 1 or Stage 2 chronic kidney disease (CKD) to at least Stage 3 is likely within a time interval, such as up to 36 months, subsequent to computing the prediction and, if such is the case, informing the care providers' decisions and renoprotective interventions to mitigate the risk and prevent or slow the progression of chronic kidney disease and concomitant morbidity in such patients.

Thus, an aim of embodiments of this disclosure relates to automatically identifying persons who are at risk for chronic kidney disease (CKD) progression to Stage 3. In some embodiments, persons at risk for CKD progression to Stage 3 may be identified through the use of serial laboratory measurements and temporal properties of multi-variable time series determined from the measurements. The measurements and predictive algorithms may provide for use in general acute-care venues and afford a degree of robustness against variations in individual physiology, comorbid diagnoses, and severity of illness. A further aim of some embodiments is to reliably distinguish between patients with stage 3-5 CKD, at first classification, whose disease (a) remained stable, (b) progressed, or (c) improved, in a quantifiable manner to enable accurate decision-making concerning optimal treatment to reduce or delay progression of CKD in those in whom it is probable within a time-horizon of up to 36 months. Some embodiments also provide a leading indicator of near-term future abnormalities, proactively notifying clinicians caring for the user and providing the care providers with sufficient advance notice to enable initiation of effective preventive or disease-modifying maneuvers.

Accordingly, in some embodiments, serial measurements are obtained of uric acid levels from a longitudinal time series of serum or plasma samples from a human subject (e.g. a patient). In one embodiment, at least four samples of serum uric acid levels are obtained, spanning the past two to five years. In some embodiments, these levels need not be obtained at regular intervals. If four or more such time series values of uric acid measurements are available, then estimates of the probability of responsiveness to the agent or multi-drug regimen may be determined from the time series. An EDTA-anticoagulated blood sample from the patient is also obtained and used to measure a level of hemoglobin A1c (HbA1c) in the blood sample. In some embodiments, the current uric acid level may be compared with an age-gender adjusted reference level of uric acid, and the HbA1c level may be compared with a reference level; further, in one embodiment, the uric acid levels or HbA1c levels may be de-noised and/or normalized to the reference levels. An annualized uric acid velocity of the patient may then be determined based on the plurality of longitudinal measurements of serum or plasma uric acid levels. The de-noised values may be combined via a multi-variable mathematical model for determining a likelihood of risk for developing CKD within 36 months. In some embodiments, the model may take the form of a logistic regression classifier. In other embodiments, the evidence-combining may be implemented via a neural network or support vector machine or other similar classification techniques. In this way, embodiments of the invention facilitate prediction classification or decision-support alert signals to be provided at logistically convenient times far enough in advance of progression to Stage 3 chronic kidney disease to allow for effective preventive intervention in a percentage of cases. Embodiments may also facilitate the automatic identification of persons likely to benefit from a disease-modifying intervention or preventive intervention regimen or program, which may be administered using a computer software routine or health care software agent, according to the patient's risk of progression. Moreover, some embodiments use commonly-available laboratory tests, which may be performed serially. Thus, the timely determining of, for example, a 36-month predicted likelihood of progression to Stage 3 CKD is performed in such a manner so as not to be unduly dependent on scarce or expensive resources.

BRIEF DESCRIPTION OF THE DRAWINGS

The present invention is described in detail below with reference to the attached drawing figures, wherein:

FIG. 3A depicts stages of CKD and corresponding estimated glomerular filtration rate;

FIGS. 5A and 5B depict examples of a graphical user interface for providing prediction models for a male and female of risk for progression to Stage 3 CKD, using an example embodiment that has been reduced to practice;

FIGS. 7A and 7B depict an example embodiment of a computer program routine for predicting likelihood of progression to STAGE 3 CKD in an individual, in accordance with an embodiment of the disclosure.

DETAILED DESCRIPTION

Figure 1A:
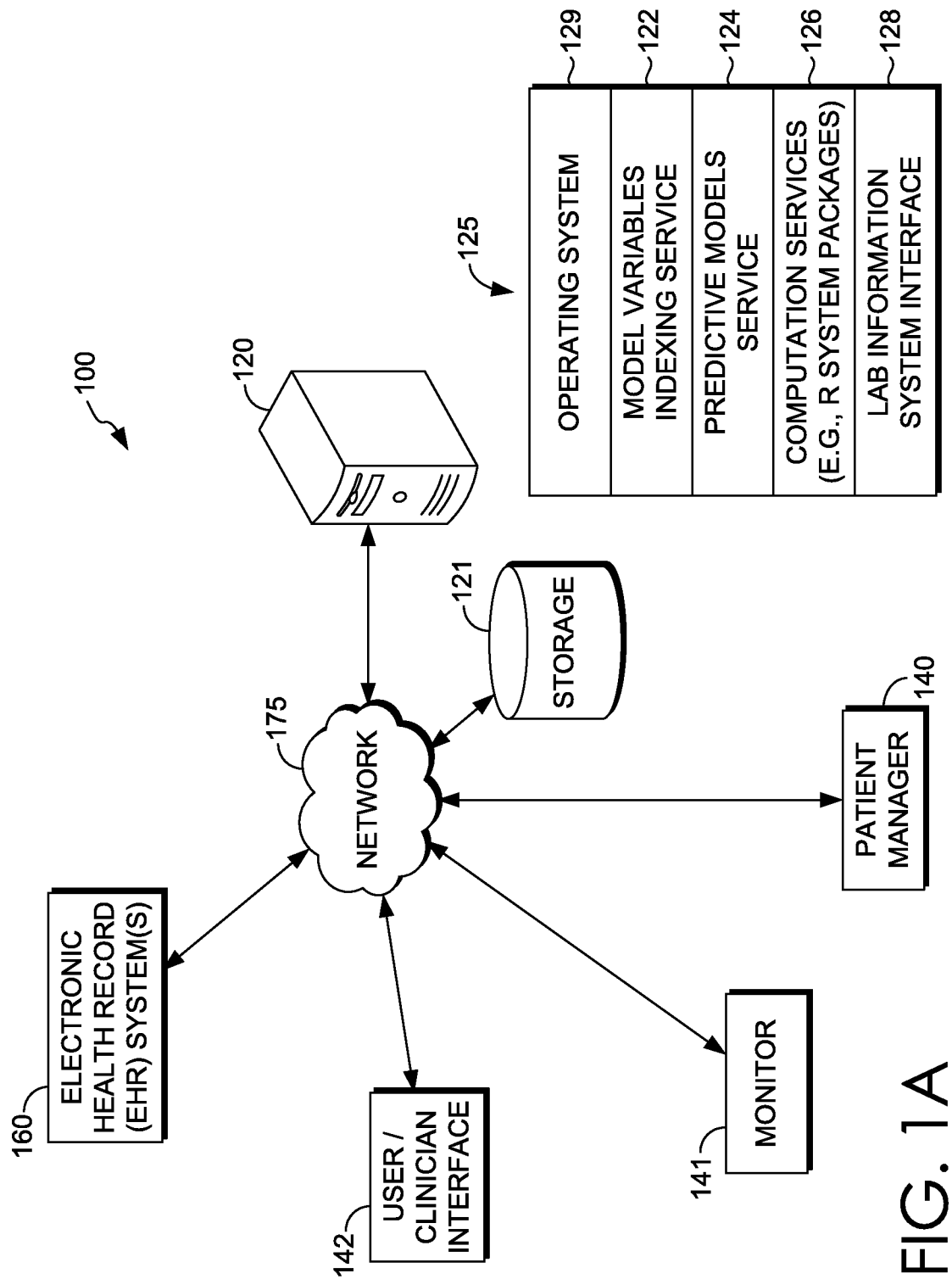
FIGS. 1A and 1B depict aspects of an illustrative operating environment suitable for practicing an embodiment of the disclosure.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of our invention may be embodied as, among other things: a method, system, or set of instructions embodied on one or more computer readable media. Accordingly, the embodiments may take the form of a hardware embodiment, a software embodiment, or an embodiment combining software and hardware. In one embodiment, the invention takes the form of a computer-program product that includes computer-usable instructions embodied on one or more computer readable media.

Computer-readable media can be any available media that can be accessed by a computing device and includes both volatile and nonvolatile media, removable and non-removable media. By way of example, and not limitation, computer-readable media comprises media implemented in any method or technology for storing information, including computer-storage media and communications media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computing device 100. Computer storage media does not comprise signals per se. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

Accordingly, at a high level, this disclosure describes, among other things, methods and systems, for identifying persons who are at risk for chronic kidney disease progression, and may include automatically identifying patients having an elevated near-term risk of chronic kidney disease progression. In particular, embodiments of the present disclosure facilitate monitoring human patients and quantitatively predicting whether or not an elevated risk of progression of Stage 1 or Stage 2 chronic kidney disease (CKD) to at least Stage 3 is likely within a time interval, such as up to 36 months. Further, if such is the case, some embodiments may facilitate informing the care provider clinicians' decisions and renoprotective interventions to mitigate the risk and prevent or slow the progression of chronic kidney disease and concomitant morbidity in such patients.

Thus, embodiments of the disclosure are directed to event prediction, risk stratification, and optimization of the assessment, communication, and decision-making to prevent, treat, and/or manage chronic kidney disease events in humans, and may take the form of a platform for embedded decision support in an electronic health record (EHR) system. In one embodiment, this includes analyzing serial laboratory measurements using commonly-available laboratory tests, such as uric acid and HbA1c. From these measurements, a multivariable time series may be determined and used for generating a multivariable mathematical model for predicting likelihood of CKD progression. The measurements and predictive algorithms may be provided for use in general acute-care venues and afford a degree of robustness against variations in individual physiology, comorbid diagnoses, and severity of illness. Some embodiments further provide a leading indicator of near-term future abnormalities, proactively notifying clinicians caring for the individual and providing the care providers with sufficient advance notice to enable initiation of effective preventive or disease-modifying maneuvers.

Moreover, unlike other approaches, some embodiments described herein may use as little as four time points, also referred to herein as serial laboratory measurements, in the time series. In particular, if four or more such time series values of uric acid measurements are available, then estimates of the probability of responsiveness to an agent or multi-drug regimen may be determined from the time series. De-noised values may be combined via a multi-variable mathematical model. In some embodiments, this may take the form of a logistic regression classifier. In other embodiments, the evidence-combining may be implemented via a neural network or support vector machine or other suitable statistical classifier or model. In each instance, embodiments of the disclosure may provide a leading indicator of near-term responsiveness to the regimen. One exemplary embodiment is integrated with case-management software and electronic health record decision-support system to facilitate decision support.

By way of example and not limitation, a user using an embodiment of the invention may be able to more confidently make decisions as to the giving or withholding of nutritional or pharmaceutical products, or other interventions. In this exemplary embodiment, the computer system may include an application that, when executed, receives user data, such as patient data, which may be received from an EHR or one or more sensors or patient monitors; calculates a plurality time series laboratory test measures; combines these in a mathematical prediction model; and communicates the composite results to a clinician-user, case-management software, decision-support systems, and/or electronic health record system(s). For example, one embodiment may notify the user in advance, via a notification message, electronic mail or alert, and may also notify the user's health plan, electronic-health record decision-support systems or personal health record systems, via a call, HTTP, SMS text-message, or other form of electronic or radiofrequency communication. The notification may indicate that the user may be likely to benefit from a disease-modifying medication regimen. This enables the care providers to take appropriate measures, including determining insurance coverage for the regimen or other aspects. For example, in one embodiment, disease-modifying medication regimen may be administered using a health care software routine or agent, which may be tailored to the particular user according to the likelihood of risk for CKD progression. Thus, one embodiment includes generating (or modifying) and executing a health care software routine or agent for administering disease-modifying medication regimen; alternatively in another embodiment computer-readable instructions may be generated and provided that enable a disease-modifying medication regimen to be carried out for the patient.

As described previously, chronic kidney disease (CKD) is increasing in epidemiologic and economic importance in developed nations, and total Medicare expenditures for CKD in 2011 exceeded $45 billion. Further, annual health spending increases with increasing severity and comorbidities, and quality of life diminishes. Therefore, it is advantageous to prevent or delay progression of CKD to the more severe, later stages—including end-stage renal disease (ESRD) at which point renal replacement therapy (dialysis or kidney transplantation) is needed.

The staging of CKD is established as shown in the graphic interface 310 of FIG. 3A, which is provided in accordance with K/DOQI and related guidelines. The prevalence of stage 3 to stage 5 CKD in 2010 was 5.9%. In patients with stage 3-5 CKD at first classification, their disease (a) remained stable, (b) progressed, or (c) improved in 2010 was approximately 50%, 10-15%, and 25-30% of patients, respectively.

CKD also exhibits significant ethnic variation in its occurrence and progression, mostly due to increased prevalence and severity of hypertension. As an example, 37% of end-stage renal disease cases in African Americans can be attributed to high blood pressure, compared with 19% among Caucasians. Treatment efficacy also differs between racial groups. Administration of anti-hypertensive drugs generally halts disease progression in white populations, but has little effect in slowing renal disease among black populations, and additional treatment such as bicarbonate therapy is often required.

Once patients at risk for progression to stage 3 CKD are identified, a variety of therapeutic modalities are available to alter the disease course in patients with CKD and slow its progression. For example, optimal diabetes therapy (HbA1c target 7%), reduction of proteinuria, aldosterone blockade, and the optimal use of ACEI/ARB antihypertensive therapies are frequently beneficial, as are following certain dietary restrictions, such as limiting dietary sodium and protein intake and body weight reduction. Proper treatment for elevated serum phosphorus and parathyroid hormone levels can delay appearance of comorbidities that exacerbate or accelerate progression of CKD. Correction of anemia with erythropoietin therapy is also beneficial in advanced CKD with hemoglobin goals in the 10-12 g/dL range. Additionally, treatment of acidosis appears to offer benefit and suggests that increasing serum bicarbonate levels to greater than 20 mmol/L is beneficial. Also, approaches to altering the course of CKD by targeting fibroblast growth factor 23 (FGF-23), transforming growth factor β (TGF-β), tumor necrosis factor alpha (TNF-α), neprilysin, and nuclear factor-erythroid-2-related factor 2 (Nrf2) level reductions also may be considered.

An approach using biomarker may enable characterizing the biological basis for the heterogeneity of individuals' clinical course and their personalized response to specific treatments, particularly in cancer. The ability to molecularly characterize human diseases presents new opportunities to develop more effective treatments and new challenges for the design and analysis of clinical trials. 'Personalized medicine' is a model for optimizing therapeutics. 'Personalization' posits that customizing the treatment for individual patients will deliver superior clinical outcomes with optimum safety and cost-effectiveness. In this model, diagnostic tests are essential for selecting the safest and most efficacious treatments and choosing the dose or administration schedule that best matches the pharmacologic and pathophysiologic particulars of the individual. The term 'companion diagnostics' may be used to describe such tests, whereby molecular assays that measure the levels of specific soluble analytes or proteins or specific gene mutations are used to provide a specific therapy for an individual by stratifying the disease status, selecting the proper medication regimen, and tailoring the dosages and administration. Companion diagnostics may be used to aid clinical decision making to identify patients who are most likely to respond to treatment and to identify patients who likely will not benefit. While some certain 'companion diagnostics' (CoDx) are univariable tests for the presence or absence of a receptor that is pertinent to the mechanism of action of the associated therapeutic, or are univariable tests for the level of one particular analyte, other CoDx's may be 'in vitro diagnostic multivariable index assays' (IVDMIAs). In this connection, multivariable phenotypic profiling can be as important as genotypic profiling in devising personalized medicine treatments.

Further, in some instances patient therapy may be improved through the identification of targets and surrogate molecular signatures that can help direct appropriate treatment regimens for efficacy and drug safety. In particular, patient biofluids or biopsy tissue are isolated and analyzed for genetic, immunohistochemical, and/or soluble markers to determine if a predictive biomarker signature (e.g., altered concentration of analyte, mutated gene product, differentially expressed protein or pattern of multiple proteins, altered cell surface antigen, etc.) exists as a means for selecting optimal treatment. These biomarkers may be drug-specific targets and/or differentially expressed nucleic acids, proteins, or cell lineage profiles that can directly affect the patient's disease tissue or immune response to a therapeutic regimen.

Improvements in diagnostics that can prescreen predictive response biomarker profiles will optimize patient therapy via molecularly-defined disease-specific treatment. Conversely, patients lacking predictive response biomarkers will no longer needlessly be exposed to drugs that are unlikely to provide clinical benefit, thereby enabling patients to pursue other therapeutic options and lowering overall healthcare costs by avoiding futile treatment. But while patient molecular profiling offers a powerful tool to direct treatment options, the difficulty in identifying disease-specific targets or predictive biomarker signatures that stratify a significant fraction within a disease indication remains challenging.

However, according to an embodiment of the disclosure, a patient can be predetermined in real-time as to whether or not their kidney disease is likely to progress to Stage 3 CKD. Despite growing success in the treatment of CKD achieved using molecular targeted therapy, resistance seems to develop to virtually all of the drugs at some point in time. One way to suppress or delay development of resistance may be through the use of combination therapy. For example, a combined regimen of an AVP V2 antagonist and a TNF-alpha inhibitor may offer synergistic benefits, compared to either therapeutic class of disease-modifying agents used separately.

Recent trends are moving away from the univariable 'one biomarker: one drug' companion diagnostic scenario, which has characterized the past two decades of targeted drug development, toward a more integrated approach with multiple biomarkers and multi-drug regimens. This 'new paradigm' will likely pave the way for the introduction of multiplexing strategies using IVDMIAs that utilize multivariable phenotyping as well as gene expression arrays and next-generation sequencing, not only for cancer treatment but for the treatment of CKD and other chronic diseases.

Advances in understanding the biology of kidney disease as well as advances in diagnostic technologies, such as the advent of affordable high-resolution DNA sequencing, have had a major impact on the approach to identification of specific alterations in a given patient's condition that could be used as a basis for CKD treatment selection and, hence, the development of companion diagnostics. Presently there are no such 'companion diagnostics' in CKD, even though there are a number of receptor-targeted medication that have annual cost-of-therapy price-tags greater than $50,000, which is sufficiently high to merit such a companion diagnostic test.

In that regard, some biomarkers that characterize the kidneys' status and rate of functional decline may serve as a guide for preventive and disease-modifying interventions to conserve kidney function in human subjects in whom CKD has not progressed beyond a certain point. Accordingly, some embodiments of the present disclosure involve just such a surrogate measure or multivariable predictor.

Patients in earlier stages of declining kidney function (Stages 1 and 2) bear increased risks for the progression to later-Stage CKD (Stages 3, 4, 5, and end-stage renal disease, or ESRD) requiring permanent dialysis therapy or renal transplantation. Thus, there is a compelling need to predict and prevent CKD efficaciously and, in those for whom prevention is not possible or successful, to undertake effective treatment of CKD as quickly as possible. In some traditional approaches, the principle clinical tools used to detect CKD were serial measurement of serum creatinine (Cr), blood urea nitrogen (BUN), certain other urine biochemical markers, and measurement of urine output volume per unit time. However, accurate prediction using such markers is unreliable based on (a) inadequate statistical sensitivity and specificity for the purpose of predicting progression of chronic kidney disease and (b) require prolonged follow-up and repeated measurements over a period of months before providing guidance as to rate of progression.

The established chronic kidney disease (CKD) progression end point of end-stage renal disease (ESRD) or a doubling of serum creatinine concentration (corresponding to a change in estimated glomerular filtration rate [GFR] of −57% or greater) is a late event. Bicarbonate concentrations are likewise a lagging indicator. But one advantage of some embodiments described herein may provide a leading indicator, which may facilitate characterizing a prognosis as well as guiding therapy so as to retard progression of CKD.

Biomarkers such as ADMA and KIM-1 recently show promise as leading indicators of CKD progression, as do soluble tumor necrosis factor receptor-1 and -2 (sTNF-R1; sTNF-R2), sFAS, TNF-alpha, interleukin-6 (IL-6), A-type natriuretic peptide (ANP), adrenomedullin (ADM), neutrophil gelatinase-associated lipocalin (NGAL), and other biomarkers. However, diagnostics based on measurement of such markers have not yet received regulatory approval and, even when approval is forthcoming, the availability of such tests may likely be limited, particularly in smaller and community-based settings. Thus, another advantage provided by some embodiments of this disclosure is to provide diagnostics that utilize biomarkers that are inexpensive and already broadly available.

The role of uric acid as a biomarker of progression of chronic kidney disease (CKD) remains controversial. Experimental and clinical studies indicate that uric acid is associated with several risk factors of CKD including diabetes, hypertension, oxidative stress, and inflammation and that hyperuricemia could be considered as a common dominator linking CKD and cardiovascular disease. Notably, the impact of serum uric acid levels on the survival of CKD, dialysis patients, and renal transplant recipients is also a matter of debate, as there are conflicting results from clinical studies. At present, there is no definite data whether uric acid is causal, compensatory, coincidental or if it is only an epiphenomenon in these patients.

Moreover, some genomics-based or proteomics-based approaches involve cumbersome, complex, expensive and/or invasive instrumentation. Yet other recently-introduced methods involve measurements, such as genomic or proteomic laboratory tests, that are not widely available and that have performance turnaround times of many hours or days before the results and prediction are available for use, such that the prediction or classification is not timely with respect to interventions aimed at preventing the predicted progression.

Accordingly, advantages of predictive and diagnostic methods according to embodiments of the disclosure described herein arise not only in prevention of CKD progression but also in its management. For example, some such embodiments constitute a specialized type of so-called 'companion diagnostics' or IVDMIAs that can help to guide optimal selection of therapeutic regimen.

In light of the foregoing, improved predictive-preventive methods and systems have been devised, and in embodiments of these methods and systems, prediction classification or decision-support alert signals emitted by the system, or according to these methods, are provided at logistically convenient times far enough in advance of progression to Stage 3 chronic kidney disease to allow for effective preventive intervention in a percentage of cases. In some embodiments, these systems and methods entail the use of commonly-available laboratory tests performed serially. For example, the timely determining of a 36-month predicted likelihood of progression to Stage 3 CKD is performed in such a manner so as not to be unduly dependent on scarce or expensive resources.

Referring now to the drawings in general, and initially to FIG. 1A in particular, an aspect of an operating environment 100 is provided suitable for practicing an embodiment of this disclosure. We show certain items in block-diagram form more for being able to reference something consistent with the nature of a patent than to imply that a certain component is or is not part of a certain device. Similarly, although some items are depicted in the singular form, plural items are contemplated as well. For instance, although storage may be illustrated as a single data store, storage may really be multiple data stores distributed across multiple locations. But because showing every variation of each item could obscure aspects of the invention, we have provided and referenced items in the singular for readability while fully contemplating, where applicable, the plural.

As shown in FIG. 1, example operating environment 100 provides an aspect of a computerized system for compiling and/or running aspects of an embodiment including predicting likelihood of progression to Stage 3 CKD. Environment 100 includes one or more electronic health record (EHR) systems, such as hospital EHR system 160, communicatively coupled to network 175, which is communicatively coupled to computer system 120. In some embodiments, components of environment 100 that are shown as distinct components may be embodied as part of or within other components of environment 100. For example, EHR systems 160 may comprise one or a plurality of EHR systems, such as hospital EHR systems, health information exchange EHR systems, ambulatory clinic EHR systems, psychiatry/neurology EHR systems, and may be implemented in computer system 120. Similarly, EHR system 160 may perform functions for two or more EHR systems (not shown).

Network 175 may comprise the Internet, and/or one or more public networks, private networks, other communications networks such as a cellular network, or similar network(s) for facilitating communication among devices connected through the network. In some embodiments, network 175 may be determined based on factors, such as the source and destination of the information communicated over network 175, the path between the source and destination, or the nature of the information. For example, intra-organization or internal communication may use a private network or virtual private network (VPN). Moreover, in some embodiments, items shown as being communicatively coupled to network 175 may be directly communicatively coupled to other items shown as being communicatively coupled to network 175.

In some embodiments, operating environment 100 may include a firewall (not shown) between a first component and network 175. In such embodiments, the firewall may reside on a second component located between the first component and network 175, such as on a server (not shown), or reside on another component within network 175, or may reside on or as part of the first component.

Embodiments of EHR system 160 include one or more data stores of health records, which may be stored on storage 121, and may further include one or more computers or servers that facilitate the storing and retrieval of the health records. In some embodiments, EHR system 160 may be implemented as a cloud-based platform or may be distributed across multiple physical locations. EHR system 160 may further include record systems that store real-time or near real-time patient (or user) information, such as wearable, bedside, or in-home patient monitors, for example.

Although FIG. 1A depicts an exemplary EHR system 160, it is contemplated that an embodiment relies on user manager or patient manager 140 and/or monitor 141 for storing and retrieving patient record information, such as information acquired from monitor 141.

Example operating environment 100 further includes provider user/clinician interface 142 communicatively coupled through network 175 to an EHR system 160. Although environment 100 depicts an indirect communicative coupling between interface 142 and EHR system 160 through network 175, it is contemplated that an embodiment of interface 142 is communicatively coupled to EHR system 160 directly. An embodiment of interface 142 takes the form of a user interface operated by a software application or set of applications on a client computing device such as a personal computer, laptop, smartphone, or tablet computing device. In an embodiment, the application includes the PowerChart® software manufactured by Cerner Corporation. In an embodiment, the application is a Web-based application or applet. A provider clinician application facilitates accessing and receiving information from a user or health care provider about a specific patient or set of patients for which the likelihood(s) of future events, such as progression to Stage 3 CKD are determined according to the embodiments presented herein. Embodiments of interface 142 also facilitate accessing and receiving information from a user or health care provider about a specific patient or population of patients including patient history; health care resource data; variables measurements, time series, and predictions (including plotting or displaying the determined outcome and/or issuing an alert) described herein; or other health-related information. Embodiments may further facilitate the display of results, recommendations, or orders, for example. In an embodiment, interface 142 also facilitates receiving orders for the patient from the clinician/user, based on the results of monitoring and predictions. Interface 142 may also be used for providing diagnostic services or evaluation of the performance of various embodiments.

An embodiment of patient manager 140 takes the form of a user interface and application, which may be embodied as a software application operating on one or more mobile computing devices, tablets, smartphones, front-end terminals in communication with back-end computing systems, laptops, or other computing devices. In an embodiment, patient manager 140 includes a Web-based application or set of applications usable to manage user services provided by an embodiment of the invention. For example, in an embodiment, patient manager 140 facilitates processing, interpreting, accessing, storing, retrieving, and communicating information acquired from monitor 141, EHR system 160, or storage 121, including candidate diagnoses or conditions determined by embodiments of the invention as described herein. In an embodiment, patient manager 140 sends a notification (such as an alarm or other indication) directly to user/clinician interface 142 through network 175. In an embodiment, patient manager 140 sends a maintenance indication to provider clinician interface 142. In one embodiment of patient manager 140, an interface component may be used to facilitate access by a user (including a clinician/caregiver or patient) to functions or information on monitor 141, such as operational settings or parameters, user identification, user data stored on monitor 141, and diagnostic services or firmware updates for monitor 141, for example.

As shown in example environment 100, in one embodiment, patient manager 140 is communicatively coupled to monitor 141 and to network 175. In an embodiment, patient monitor 141 communicates, via network 175, to computer system 120 and/or user/provider clinician interface 142.

An embodiment of patient monitor 141 (sometimes referred to herein as an patient-interface component) comprises one or more sensor components operable to acquire clinical or physiological information about a patient, such as various types of physiological measurements, physiological variables, or similar clinical information associated with a particular physical or mental state of the patient, and that may be acquired periodically or as one or more time series. In one embodiment, monitor 141 comprises sensors for obtaining and analyzing the serial measurements of serum or plasma samples and/or an EDTA-anticoagulated blood sample and a blood sample measuring a level of HbA1c. In some embodiments, monitor 141 comprises a patient bedside monitor, such as those used in hospitals. In an embodiment, one or more sensor components of monitor 141 may comprise a user-wearable sensor component or sensor component integrated into the patient's environment. Examples of sensor components of monitor 141 include a sensor positioned on an appendage (on or near the user's head, attached to the user's clothing, worn around the user's head, neck, leg, arm, wrist, ankle, finger, etc.); skin-patch sensor; ingestible or sub-dermal sensor; sensor component(s) integrated into the user's living environment (including the bed, pillow, or bathroom); and sensors operable with or through a smartphone carried by the user, for example. It is also contemplated that the clinical or physiological information about patient, such as the monitored variables and/or clinical narratives regarding the patient, used according to the embodiment of the invention disclosed herein may be received from human measurements, human observations, or automatically determined by sensors in proximity to the patient. For example, in one embodiment, a nurse periodically measures a patient's blood pressure and enters the measurement and/or observations via patient manager 140 or user/clinician interface 142. In another example, a nurse or caregiver enters one or more progress notes for a patient via patient manager 140 or user/clinician interface 142. Similarly, values for serial measurements of urine osmolality and serum sodium concentration may be entered via manager 140 or interface 142.

Examples of physiological variables monitored by monitor 141 can include uric acid and HbA1c levels, as described here. Additionally, in some embodiments physiological variables monitored by monitor 141 may include, by way of example and not limitation, heart rate, blood pressure, oxygen saturation ($SO_2$), central venous pressure, other vital signs or any type of measureable, determinable, or observable physiological or clinical variable or characteristic associated with a patient, which, in some embodiments, may be used for forecasting a future value (of the measured variable, a composite variable based on one or more measured variables, or other factor determined at least in part from one or more measured variables) of a patient in order to facilitate clinical decision making In an embodiment, a monitor, such as monitor 141, comprises a sensor probe, such as an EEG probe, and a communication link that periodically transmits identification information and probe data to patient manager 140, so that the time series of monitored values is stored on patient manager 140, enabling the patient manager to form a raw binary alarm indication and/or a physiological variable decision statistic. In an embodiment, patient monitor 140 collects raw sensor information, such as optical sensor 184, and performs signal processing, such as velocity measurement, forming a physiological variable decision statistic, cumulative summing, trending, wavelet processing, thresholding, computational processing of decision statistics, logical processing of decision statistics, pre-processing or signal condition, etc., part or all of which may be performed on monitor 141, patient manager 140, user/clinician interface 142, and/or computer system 120.

An embodiment of monitor 141 stores user-derived data locally or communicates data over network 175 to be stored remotely. In an embodiment, patient manager 140 is wirelessly communicatively coupled to monitor 141. Patient manager 140 may also be embodied as a software application or app operating on a user's mobile device. In an embodiment, patient manager 140 and monitor 141 are functional components of the same device, such as a device comprising a sensor and a user interface. In an embodiment, patient manager 140 is embodied as a base station, which may also include functionality for charging monitor 141 or downloading information from monitor 141.

Computer system 120 comprises one or more processors operable to receive instructions and process them accordingly and may be embodied as a single computing device or multiple computing devices communicatively coupled to each other. In one embodiment, processing actions performed by computer system 120 are distributed among multiple locations, such as one or more local clients and one or more remote servers, and may be distributed across the other components of example operating environment 100. For example, a portion of computing system 120 may be embodied on monitor 141 or manager 140 for performing signal conditioning of the measured patient variable(s). In one embodiment, system 120 comprises one or more computing devices, such as a server, desktop computer, laptop, or tablet, cloud-computing device or distributed computing architecture, a portable computing device such as a laptop, tablet, ultra-mobile P.C., or a mobile phone.

Embodiments of computer system 120 include computer software stack 125, which, in some embodiments, operates in the cloud, as a distributed system on a virtualization layer within computer system 120, and includes operating system 129. Operating system 129 may be implemented as a platform in the cloud, which may be capable of hosting a number of services such as 122, 124, 126, and 128. Some embodiments of operating system 129 comprise a distributed adaptive agent operating system. Embodiments of services 122, 124, 126, and 128 run as a local or distributed stack in the cloud, on one or more personal computers or servers such as computer system 120, and/or a computing device running user/clinician interface 142. In some embodiments, user/clinician interface 142 operates in conjunction with software stack 125.

In embodiments, model variables indexing service 122 provide services that facilitate retrieving frequent itemsets, extracting database records, and cleaning the values of variables in records. For example, model variables indexing service 122 may perform functions for synonymic discovery, indexing or mapping variables in records, or mapping disparate health systems' ontologies, such as determining that a particular medication frequency of a first record system is the same as another record system. In some embodiments, these services may invoke computation services 126. Predictive models service 124, in general, is responsible for providing multivariable models for predicting CKD, such as described in connection to method 200 of FIG. 2.

Computation services 126 perform statistical software operations and include statistical calculation packages such as, in one embodiment, the R system (the R-project for Statistical Computing, which supports R-packages or modules tailored for specific statistical operations, and which is accessible through the Comprehensive R Archive Network (CRAN) at http://cran.r-project.org) or similar services. In an embodiment, computation services 126 and predictive models service 124 include the services or routines, which may be embodied as one or more software agents or routines such as the example embodiments of computer program routines illustratively provided in FIGS. 7A-7B.

In one embodiment, computation services 126 comprises a model solver service for determining a probability (likelihood of progression to Stage 3 CKD) using the model(s) determined by predictive models service 124. For instance, where a logistic model (logistic regression classifier) is utilized, computation services 126 may comprise a logistic model solver. Thus for example, using a predictive model determined according to the computer routine provided in FIGS. 7A and 7B, which uses the generalized linear models function glm( ) operating on a number of variable coefficients, the probability P, as solved by computation services 126, may be expressed as, $P=\exp(z)/[1+\exp(r)]$, where r is a string of variable coefficients operated on by the glm( ) function; for instance, the variables for age, estimated glomerular filtration rate (eGFR), HbA1c, and uric-acid related variables shown in FIG. 4A.

In some embodiments, computation services 126 use an EHR or lab information system interface 128, which provides serial measurements of uric acid and measurement of HbA1c or other physiological variables. Some embodiments of stack 125 may further use Apache Hadoop and Hbase framework (not shown), or similar frameworks operable for providing a distributed file system and, in some embodiments, facilitate access to cloud-based services, such as those provided by Cerner Healthe Intent®. Additionally, some embodiments of stack 125 may further comprise one or more stream processing service(s) (not shown). For example, such stream processing service(s) may be embodied using IBM InfoSphere stream processing platform, Twitter Storm stream processing, Ptolemy or Kepler stream processing software, or similar complex event processing (CEP) platforms, frameworks, or services, which may include the user of multiple such stream processing services operating in parallel, serially, or independently. Some embodiments of the invention also may be used in conjunction with Cerner Millennium®, Cerner CareAware® (including CareAware iBus®), Cerner CareCompass®, or similar products and services.

Example operating environment 100 also includes storage 121 (or data store 121), which in some embodiments includes patient data for a candidate or target patient (or information for multiple patients), including raw and processed patient data; variables associated with patient recommendations; recommendation knowledge base; recommendation rules; recommendations; recommendation update statistics; an operational data store, which stores events, frequent itemsets (such as "X often happens with Y", for example), and itemsets index information; association rulebases; agent libraries, solvers and solver libraries, and other similar information including data and computer-usable instructions; patient-derived data; and health care provider information, for example. It is contemplated that the term 'data' includes any information that can be stored in a computer-storage device or system, such as user-derived data, computer usable instructions, software applications, or other information. In some embodiments, data store 121 comprises the data store(s) associated with EHR system 160. Further, although depicted as a single data store, data store 121 may comprise one or more data stores, or may be in the cloud.

Figure 1B:
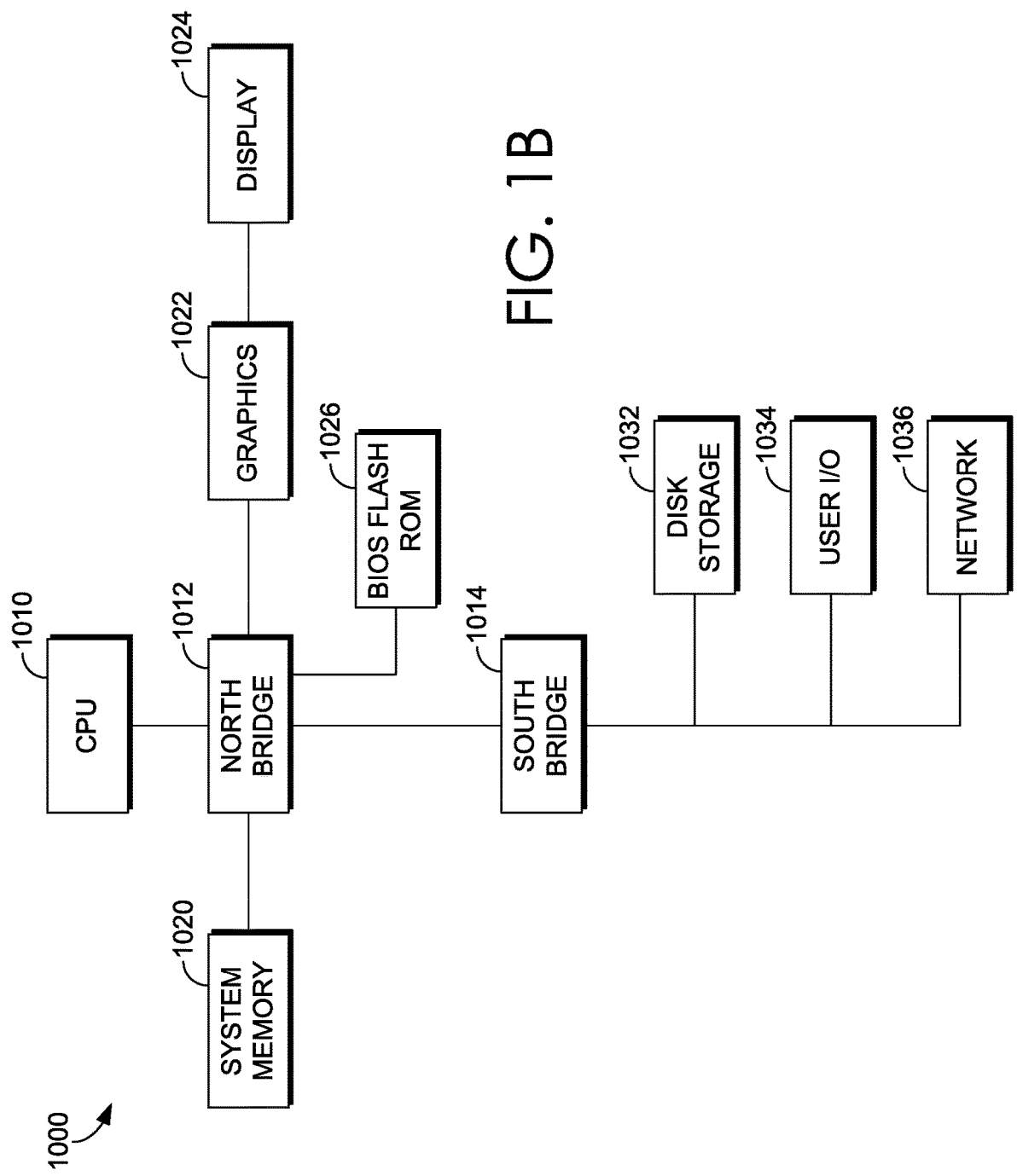

Turning briefly to FIG. 1B, there is shown one example embodiment of computing system 1000 that has software instructions for storage of data and programs in computer-readable media. Computing system 1000 is representative of a system architecture that is suitable for computer systems such as computing system 120. One or more CPUs, such as CPU 1010, have internal memory for storage and are coupled to the north bridge device 1012, allowing CPU 1010 to store instructions and data elements in system memory 1020, or memory associated with graphics card 1022, which is coupled to display 1024. Bios flash ROM 1026 also couples to north bridge device 1012. South bridge device 1014 connects to north bridge device 1012 allowing CPU 1010 to store instructions and data elements in disk storage 1032 such as a fixed disk or USB disk, or to make use of network 1036 for remote storage. One or more user I/O devices 1034, such as a communication device, a mouse, a touch screen, a joystick, a touch stick, a trackball, or keyboard, couples to CPU 1010 through south bridge 1014 as well. The system architecture depicted in FIG. 1B is provided as one example of any number of suitable computer architectures, such as computing architectures that support local, distributed, or cloud-based software platforms, and are suitable for supporting computing system 120.

Returning to FIG. 1A, in some embodiments, computer system 120 is a computing system made up of one or more computing devices. In some embodiments, computer system 120 includes one or more software agents, and in an embodiment includes an adaptive multi-agent operating system, but it will be appreciated that computer system 120 may also take the form of an adaptive single agent system or a non-agent system. Computer system 120 may be a distributed computing system, a data processing system, a centralized computing system, a single computer such as a desktop or laptop computer or a networked computing system.

Figure 2:
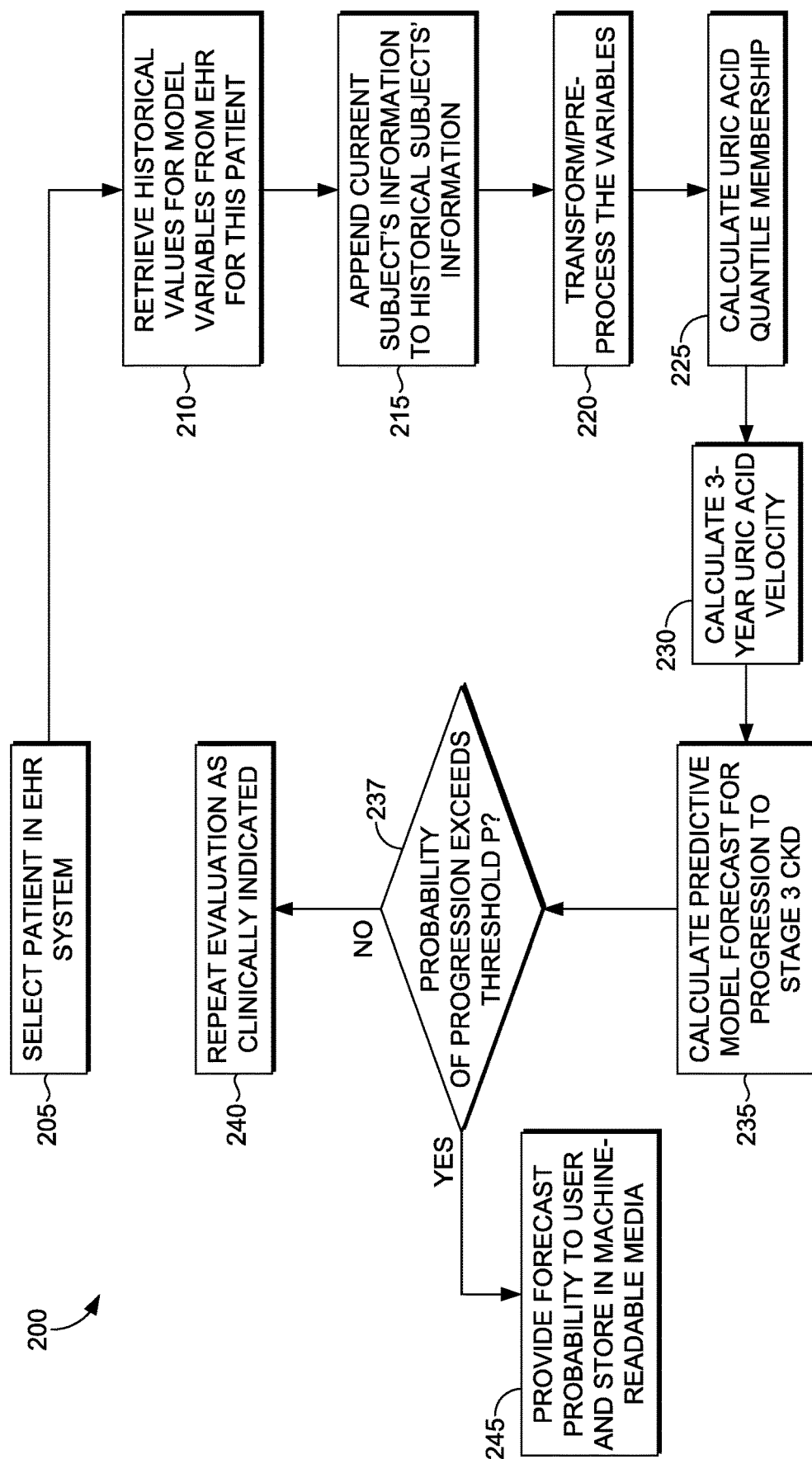
FIG. 2 depicts a flow diagram of a method for predicting risk of progression to Stage 3 CKD in an individual, in accordance with an embodiment of the disclosure.

Turning now to FIG. 2, one example embodiment of a method for predicting progression to Stage 3 CKD is provided and referred to generally as method 200. At step 205, a candidate patient is identified (e.g. selected) in an EHR system. In the example embodiment of method 200, the candidate patient will be evaluated to determine a risk of progressing to Stage 3 CKD over the next 36 months. At step 210, historical values for model variables for this candidate patient are received. The historical values may be received from an HER associated with the candidate patient. The historic values may reflect variable levels measured over the past two to five years and do not need to be measured at specific intervals. In one embodiment, the specific model variables may comprise age, eGFR, serum uric acid level(s), HbA1c level(s), for example, and may depend on the particular model used. In particular, through modeling and analysis, certain parameters have been determined to be accurate predictors (e.g., age, eGFR and time-series trends in that, HbA1c, etc.).

At step 215, the candidate patient's information may be appended to the historical information. Thus, embodiments of step 215 determine a time series comprising historical and current (or recent) patient information. In some embodiments, step 215 further comprises measuring the patient's current information (e.g. measuring or determining current values for the model variables). For example, an analysis of the patient's blood may be used to determine uric acid level. In some embodiments, monitor 141 facilitates determining current values of physiological model parameters for the candidate patient.

At step 220, the variables are pre-processed and/or transformed. Embodiments of step 220 may transform the model parameters to reflect strong nonlinearities, such as relationships of the variables' values according to age or gender. Examples of the transformed variables are shown in the risk model structures depicted in FIG. 4A, and include age, eGFR, HbA1c, and variables related to uric acid levels. For instance, during pre-processing, age may be transformed using a logistical model. Additionally, a minimum/maximum transformation of eGFR may be performed. In one embodiment, the reference minimum eGFR is 61 mL/min/ 1.732 $m^2$ of body surface area and the reference maximum eGFR is 120 mL/min/1.732 $m^2$ of body surface area. Additionally, transformation may include a thresholding of HBA1c. In one embodiment, for instance, it is determined whether a patient's HBA1c level is greater than 8.5%.

At step 225, uric acid quantile membership is determined. In some embodiments, percentile memberships, rather than quantile memberships may be determined. An example of such variable transformations and quantile memberships are illustratively provided in the comments of the computer code of FIG. 7A. In particular, looking only at numeric levels of uric acid (as opposed to what quantile or percentile the candidate patient is in and/or the patient's gender), may effectively, statistically obfuscate the patterns or trends indicating CKD progression. However, the transformation/ pre-processing and determining quantile (or percentile) membership and/or stratifying the models by gender enable identification of the CKD progression (via the appropriate model) much more readily.

Figure 3B:
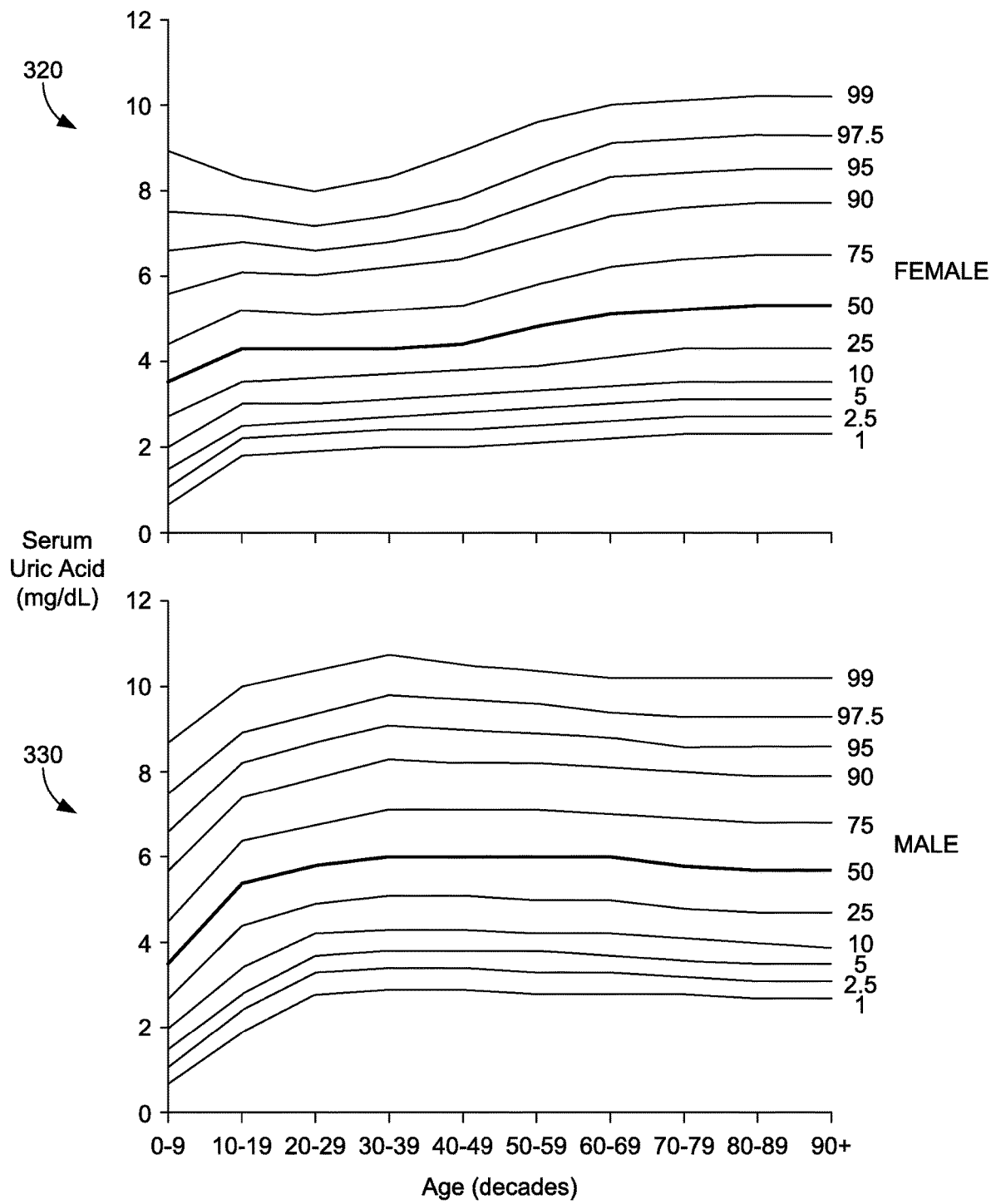
FIG. 3B depicts a graphic representation of quantiles of serum uric acid levels by age and gender for use in accordance with an embodiment of the disclosure.

Turning briefly to FIG. 3B, example quantiles of serum uric acid levels by age and gender are depicted. A graphical illustration of quantiles for females 320 and a graphical illustration of quantiles for males 330 are both provided. The uric acid levels may be determined using routine testing, such as using a Chem-21 blood test. Interestingly, it can be seen that males during puberty have higher uric acid levels than females during puberty. The uric acid level for most of women's lives average around 4 mg/dL, while the level for men's lives average around 5 mg/dL. Additionally, higher levels of uric acid may yield symptoms of gout. In an example embodiment of the invention reduced to practice, the quantiles shown in FIG. 3B were determined from de-identified patient data for over one million patients. The time and gender related trends determined from this information may be applied to the model such that the model is made dependent on what percentile a candidate patient is in or how that percentile placement changes over a period of 2-5 years. In some embodiments, during transformation/pre-processing, a candidate patient's uric acid levels are compared to values of levels in a stored references table that separates levels by gender and age (for example, by age in decades), and if the candidate patient's uric acid exceeds the corresponding level in the look up tables, a value of 1 is used as input for the uric acid level for calculating the risk.

Figure 4A:
FIG. 4A depicts example structures of prediction models for risk of progression to Stage 3 CKD by gender, in accordance with an embodiment of the disclosure.
Figure 4B:
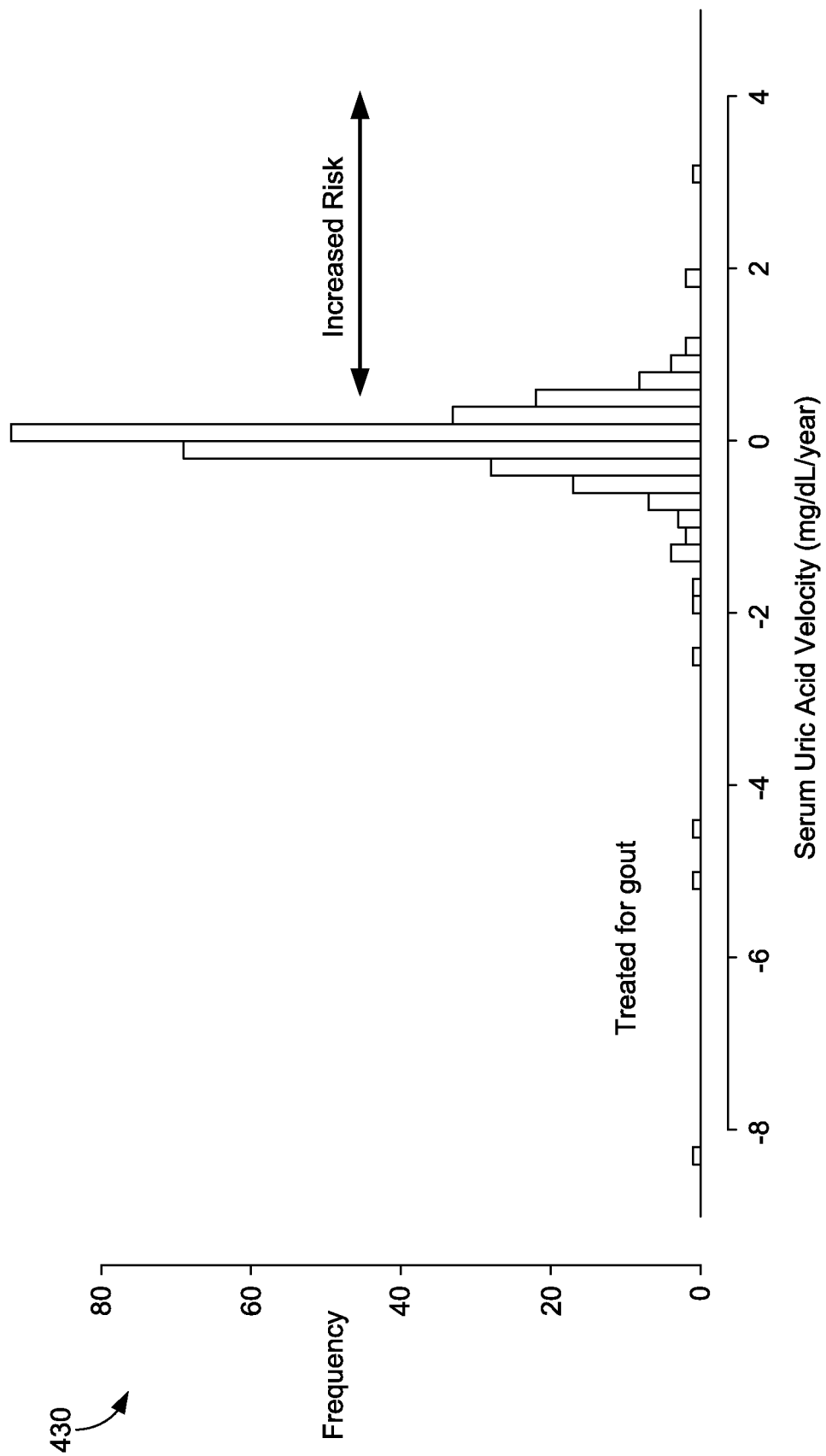
FIG. 4B depicts a graphic representation of uric acid velocity distribution, in accordance with an embodiment of the disclosure.

Returning to FIG. 2, at step 230, a uric acid velocity is determined. In the example embodiment of method 200, uric acid velocity (e.g., mg/dL/year or the change in concentration per year) is determined over a three-year duration (most recent three years). Turning briefly to FIG. 4B, a distribution of uric acid velocity is shown in mg/dL/year. The histogram of FIG. 4B shows, on the left-hand side, very low velocity levels resulting from individuals treated for gout as the levels may be decreasing over time. Because a goal of the prediction provided by method 200 is reliability, in some embodiments of method 200, a floor is used such that levels corresponding to individuals treated for gout are not included. In some embodiments, the floor is set to zero velocity.

At step 235, a predictive model forecast for progression to Stage 3 CKD is determined. Embodiments of step 235 determine the probability P, such as described in the example in connection with computation services 126 in FIG. 1A. In an embodiment, the probability of eGFR of less than 60 (which corresponds to Stage 3 CKD of higher) within 36 months is determined. In one embodiment, a series of one or more multi-variable logistic regressions is applied to estimate probability of CKD developing within 36 months. Examples of the probability determined in step 235, as determined for the same variable inputs for a model for a human female and a human male, are shown in example graphic interfaces of FIGS. 5A and 5B, respectively. In particular, the graphic interface 510 of FIG. 1A shows a probability of 37% for the female, and the graphic interface 520 of FIG. 5B shows a probability of 97% for a male, given the same variable input values for the model (as shown in the upper-cell fields of FIGS. 5A and 5B). An example embodiment of a computer routine for carrying out steps 225, 230, and 235 of method 200 is illustratively provided in FIGS. 7A and 7B. It is contemplated, however, that other means may be used for determining the statically relationship between the input input biomarker variables and the outcome of development of Stage 3 CKD within the forecasting time period, such as support vector machine, random forest, gradient boosting, or classification and regression tree (CART) methods. In some embodiments, a plurality of these methods may be used and the results for each may be combined for an ensemble model to determine the forecast probability. For example, the ensemble model may include calculating a majority vote among a plurality of sub-models, or may include combining outputs for each sub-model by calculating an arithmetic mean or medium of the outputs.

At step 237, the forecast probability (also referred to herein as calculated probability) is evaluated against a threshold probability to determine whether there is a risk for progression to Stage 3 CKD with a future time interval, such as 36 months. In other embodiments, the future time interval may comprise a range between one and ten years, including three to five years. In some aspects, a risk for progression to Stage 3 CKD is found when the forecast probability satisfies a threshold. For example, in one embodiment, a risk may be found when the forecast probability exceeds the threshold probability. Where a risk for progressing to Stage 3 CKD is found to exist for the candidate patient, method 200 proceeds to step 245. If no such risk is determined, then method 200 proceeds to step 240. In embodiments of step 237, the threshold probability may be predetermined by a clinician or healthcare provider or may be determined by empirically. The predetermined threshold may be based on how prevalent kidney-related spending is for a particular health care entity and, thus, could reflect a discretionary financial decision, in an embodiment. The predetermined threshold probability could also be context dependent; for instance, where a particular patient has a family history of CKD, then a lower threshold, such as a probability of greater than 0.3, may be used.

At step 240, where the threshold of step 237 was not exceeded, the evaluation may be repeated for the candidate patient as clinically indicated. This may vary based on other factors or conditions of the patient; for example, if the patient has another disease such as heart disease or has a greater risk for CKD, then the evaluation may be repeated more often (e.g. every 6 months, rather than every year). However, if the patient is younger, such as being in his or her twenties, and has lower risk for CKD, then the evaluation may be repeated whenever the next visit with a caregiver occurs, which may be in 5 years.

At step 245, the forecast probability is provided. In one embodiment, a notification or alert is issued to a caregiver indicating that the patient has a risk for progression to Stage 3 CKD. In some embodiments, the notification may further indicate the specific probability or may indicate a category or other label characterizing the probability value (e.g., high risk, moderate risk). Some embodiments of step 245 may further include automatically ordering further testing, scheduling clinic visits for further longitudinal monitoring, orders for kidney-protective medications, or other interventions. In some embodiments, a disease-modifying medication and/or therapeutic regimen may be scheduled and/or administered using a health care software routine or agent, which may be tailored to the particular user according to the likelihood of risk for CKD progression. Thus, an embodiment includes generating (or modifying) and executing a health care software routine or agent for administering disease-modifying medication regimen; alternatively in another embodiment computer-readable instructions may be generated and provided that enable a disease-modifying medication regimen to be carried out for the patient.

With reference to FIGS. 4A-6B, and continuing reference to method 200 of FIG. 2, an example is provided of one embodiment of the invention reduced to practice for time series multivariable properties-based prediction and prevention of CKD progression. In this example, records were retrieved from a patient health records data warehouse, which is derived from Cerner electronic health records (EHR) from 100% of episodes of care that are incident upon the participating health institutions. The personally-identifiable information was removed in conformance with U.S. HIPAA law and regulations, and the de-identified data were stored in a separate, secure database. A total of 360 ambulatory patients' records contained 4 or more date-time stamped values for each of a variety of laboratory and physiologic parameters that were contemporaneous with the nephrology clinic episodes.

The large observational EHR-derived, de-identified datasets such as Cerner Health Facts® data warehouse provided the resources to enable (a) determination of context-specific regimens that are safe and effective in delaying progression to Stage 3 CKD and (b) development of predictive mathematical models that identify who will benefit from disease-preventive or disease-retarding regimens and who will not.

In this embodiment reduced to practice, the staging of CKD was established as shown in FIG. 3, which is in accordance with K/DOQI and related guidelines.

In some embodiments, a logistic transformation was performed on age, to account for the nonlinear relationship of advanced age on residual renal reserve and rapidity of further decline in kidney function; a difference-equation transformation was performed on eGFR to account for proximity of current eGFR to the threshold for ascertaining onset of Stage 3 CKD (eGFR <60 mL/min/1.73 m2); and a logistic transformation was performed on HbA1c to account for the nonlinear relationship of diabetes and protein glycosylation to deterioration of renal function. In one embodiment, these transformations are carried out as described in connection to step 220 of FIG. 2.

Uric acid level quantiles, such as described in step 225 of method 200, were determined by age groups, each spanning ten years, for each gender from records from 1,024,187 individuals with serum uric acid levels in the Cerner Health Facts® data warehouse and, using these quantiles, a derived variable was constructed denoting 4th-quartile status of the most recent of four uric acid values in a time series of uric acid determinations for each patient.

Using the foregoing variables, the glm( ) function of the R-system was used (as shown in the example computer routine of FIGS. 7A and 7B) to construct two logistic regression predictive models for the association of the input biomarker variables with future emergence of Stage 3 CKD with a forward time-horizon of 36 months. One model was constructed for females, and one model was constructed for males. FIG. 4A depicts an aspect of the example model constructed for females 410 and an aspect of the example models constructed for males 420. The aspects provided show the variables determined to be statistically significant (e.g. probability >0.05) for predicting progression of Stage 3 CKD. The models include an "estimate" that comprises estimates of the coefficients for the model variables. The example models of FIG. 4A also include columns for standard error of the estimates, z-values, and probability, where the number of asterisks indicates statistical significance.

Figures 6A, 6B:
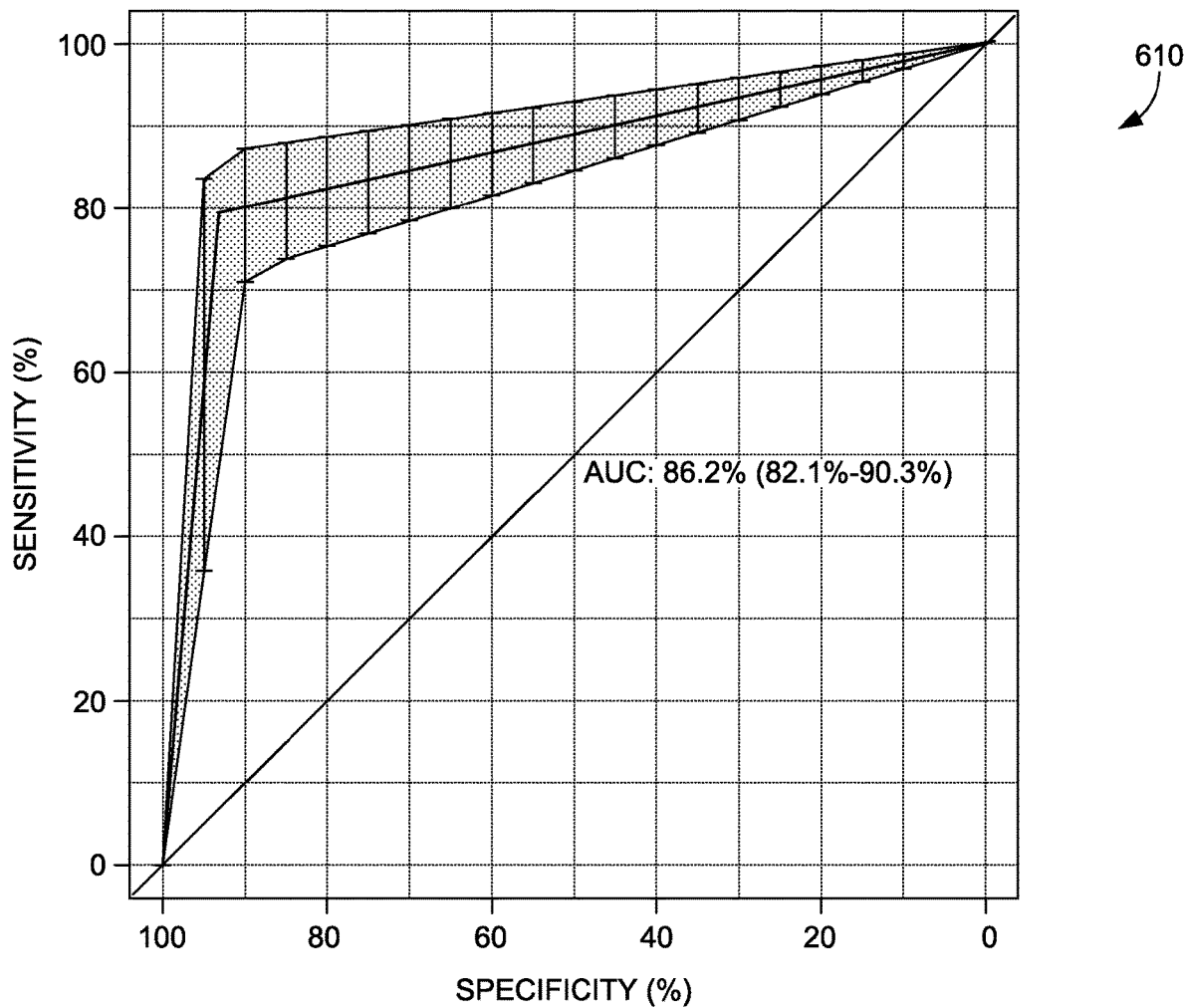
FIGS. 6A and 6B depicts a Receiver Operating Characteristic (ROC) curve representing the accuracy and discriminating classificatory capacity, and the statistical performance of an exemplary embodiment reduced to practice using a cohort of 49 subjects.

In FIG. 6A, a ROC curve 610 is shown from an analysis performed to compare the efficacy of the aspect of the present disclosure reduced to practice. As shown, the ROC area under the curve in the final composite model was 0.862. FIG. 6B depicts a graphical representation 620 showing the corresponding statistical performance of the composite model.

The as-treated dataset contained measurements of the parameters that arose in the course of conventional ordering practices in an ambulatory clinic setting. Electrolytes, blood urea nitrogen, serum creatinine, serum uric acid, and blood HbA1c were routinely measured on each clinic visit, which occurred at approximately annual intervals.

These temporal patterns are of such complexity and variability that it would be beyond the capability of a human being to examine the values of the laboratory results for urine osmolality tests and to determine a uric acid velocity or to predict progression to Stage 3 CKD that has not yet materialized. Through some embodiments of this disclosure, it is shown that temporal changes in age-gender adjusted uric acid quantile and in uric acid velocity—either jointly or separately—can serve as a reliable composite leading indicator of subsequent progression to Stage 3 CKD.

Another aspect of the disclosure concerns (a) the determining of at least one temporal property of the uric acid time series, such as percentage change from baseline or velocity, (b) the transformation of the age in decades and the biomarker values to numerical scores, (c) the combining of the evidence via a multivariable predictive model, such as a logistic regression equation, to form a quantitative probability of Stage 3 CKD materializing within a subsequent time interval, and (d) the rendering of the predicted probability to one or more human decision-makers in the context of an electronic health record information system.

Figure 8:
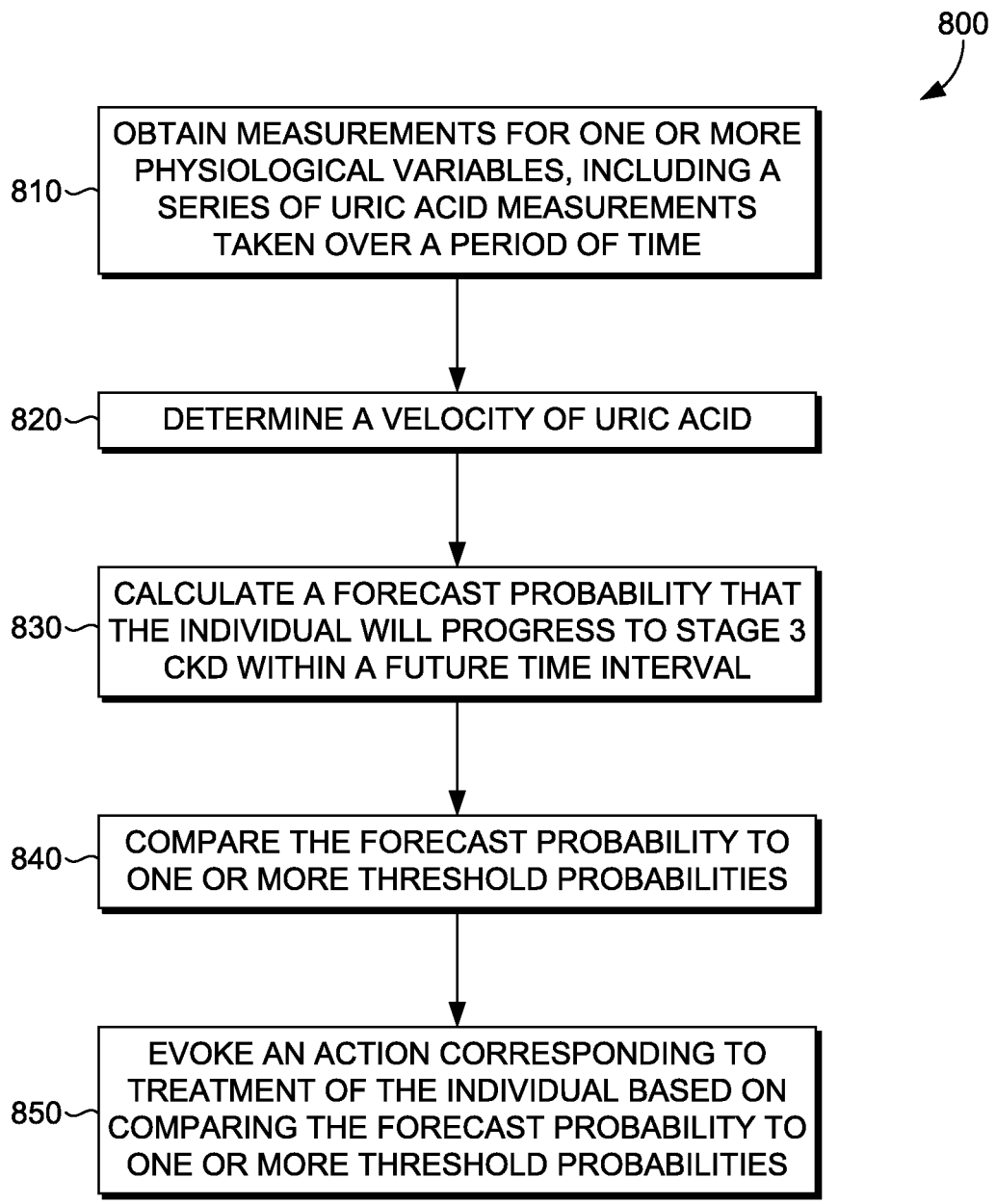
FIGS. 8-9 depict flow diagrams of methods for predicting an individual's risk of progression to Stage 3 CKD, in accordance with embodiments of the present disclosure.

Turning now to FIG. 8, a block diagram of method 800 for predicting progression to Stage 3 of CKD in an individual is provided, in accordance with an embodiment of the present disclosure. At step 810, measurement for one or more physiological variables for the individual are obtained. The physiological variables may include a series of historical uric acid measurements taken over a period of time such as, for example, the previous two to five years. The physiological variables may also include current uric acid levels, eGFR, and HbA1c levels. These measurements may be obtained a serum or plasma samples and/or EDTA-anticoagualted blood samples from the individual. At step 820, a velocity of uric acid may be determined from the series of historical measurements of uric acid. In some aspects, additional physiological variables, including the current uric acid levels, eGFR, and HbA1c levels undergo transformation and/or pre-processing.

Next, at step 830, a forecast probability that the individual will progress to Stage 3 CKD within a future time interval is calculated. In some aspects, the future time interval is 36 months, and Stage 3 CKD is defined as persistent value of eGFR or measured glomerular filtration rate (GFR) less than 69 mL/min/1.73 $m^2$ of body surface area. The forecast probability may be compared to one or more threshold probabilities, at step 840. The threshold probabilities may be predetermined by a medical professional or medical care provider or be empirically based. At step 850, based on the comparison, an action corresponding to treatment of the individual may be evoked. In some embodiments, an action is evoked when the forecast probability satisfies a threshold probabilities by, for example, exceeding the threshold probability. The action invoked may include automated invocation of action, such as initiation of prescriptions or orders, designed to prevent and/or manage CKD based on the determined probability. Such actions may include initiating a signal that causes an alert to be presented to a medical professional; initiating a signal for a plan of care to be initiated for the individual; preparing a treatment plan for the individual; automatically scheduling a caregiver to provide therapeutic treatment to the individual; modifying or generating a medical care computer program for treating the individual; an setting a schedule for future evaluations of the individual.

Figure 9:
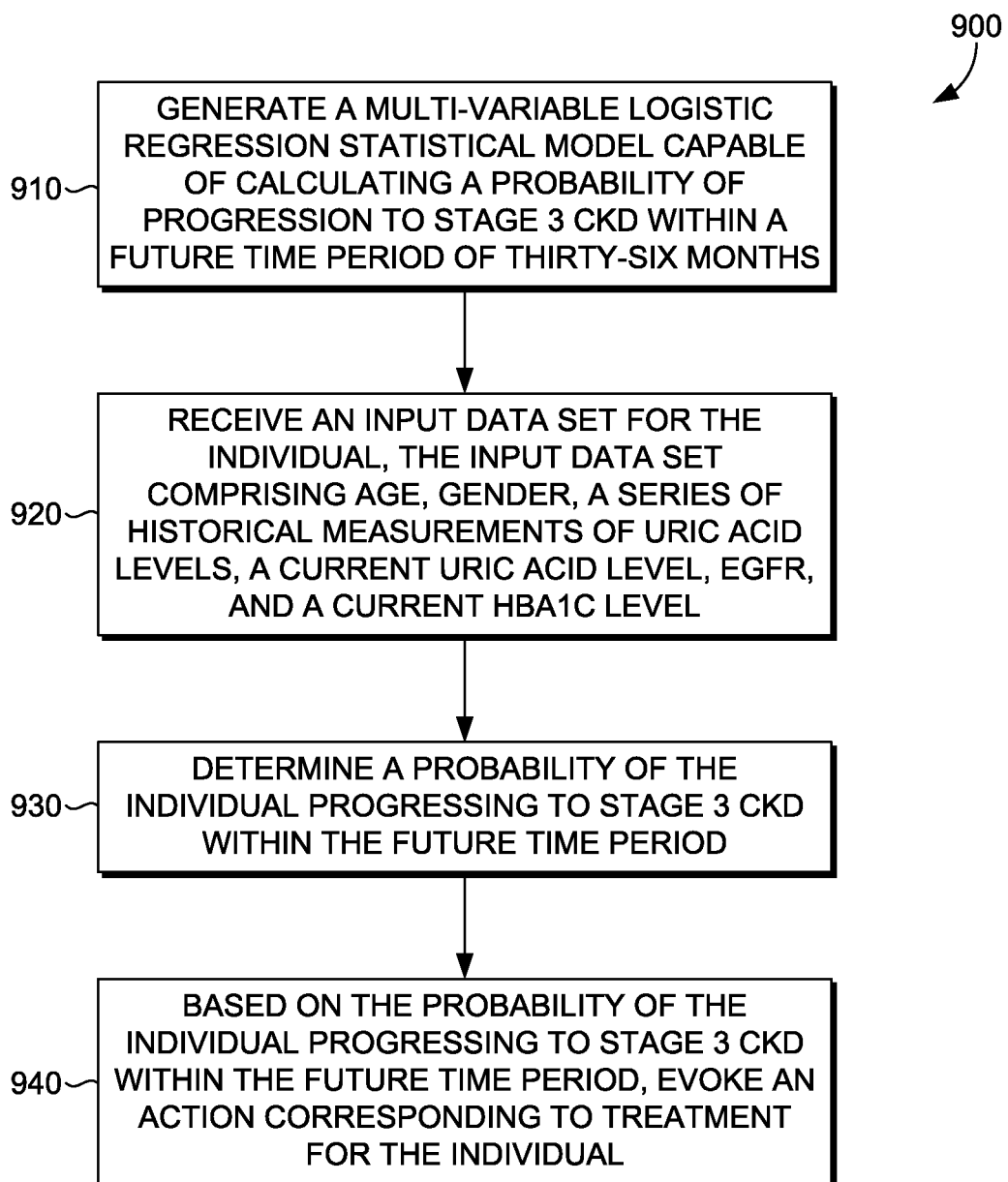

Turning now to FIG. 9, a block diagram of a method 900 for predicting progression to Stage 3 of CKD in an individual is provided, in accordance with an embodiment of the present disclosure. At step 910, a multi-variable logistic regression statistical model may be generated. The multi-variable logistic regression statistical model generated may be capable of calculating a probability of progression to Stage 3 CKD within a future time interval of 36 months. This multi-variable logistic regression statistical model may be generated using a reference data set from a population of patients, the reference data set may include measurements for various physiologic variables, such as uric acid, HbA1c, and eGFR. In some aspects, the multi-variable logistic regression statistical model is gender-specific such that one model may be used for predicting Stage 3 CKD progression in females and a second model may be used for predicting Stage 3 CKD progression in males. Accordingly, some embodiments include generating two multi-variable logistic regression models: one for males and one for females.

Continuing with method 900, at step 920, an input data set for the subject individual may be received. The input data may include, among other things, the individuals age and gender, a series of historical measurements of uric acid levels, a current uric acid level, eGFR, and HbA1c level. A velocity of uric acid for the subject individual may be determined from the series of historical measurements. Further, the current uric acid level, EGFR, and HbA1c level may be pre-processed or transformed via thresholding or other mathematical transformation process. At step 930, based on the input data set and the multi-variable logistic regression model, probability of the individual progression to Stage 3 CKD within the future time interval may be determined. At step 940, an action correspond to treatment for the individual may be evoked based on the probability of the individual progression to Stage 3 CKD within the future time interval. The action may include interventions for preventing and/or managing progression of CKD based on the determined probability, such as those described with respect to FIG. 8.

Embodiment 1: Computer storage media having computer-executable instructions embodied thereon that, when executed, facilitate a method for determining that an individual is at risk of onset of Stage 3 chronic kidney disease (CKD). The method comprises: obtaining measurements for one or more physiological variables for the individual, the measurements including at least a series of uric acid measurements for the individual taken over a period of time; determining a velocity of uric acid based on the series of uric acid measurements; calculating a forecast probability that the individual will progress to Stage 3 CKD within a future time interval based on at least the velocity of uric acid; comparing the forecast probability to one or more threshold probabilities; and evoking an action corresponding to treatment of the individual based on comparing the forecast probability to one or more threshold probabilities.

Embodiment 2: The computer storage media of embodiment 1, wherein the forecast probability is calculated using a multi-variable logistic statistical regression model.

Embodiment 3: The computer storage media of any of embodiments 1-2, wherein the future time interval is 36 months.

Embodiment 4: The computer storage media of any of embodiments 1-3, wherein the measurements for the one or more physiological variables further include a current uric acid level, an estimated glomerular filtration rate (eGFR), and a hemoglobin A1 c (HbA1c) level.

Embodiment 5: The computer storage media of any of embodiments 1-4, wherein the method further comprises transforming or pre-processing one or more measurements for the one or more physiological variables prior to calculating the forecast probability.

Embodiment 6: The computer storage media of any of embodiments 1-5, wherein the action based on the forecast probability is evoked upon determining the forecast probability satisfies the one or more threshold probabilities.

Embodiment 7: The computer storage media of any of embodiments 1-5, wherein the action evoked based on the forecast probability comprises at least one of: initiating a signal that causes an alert to be presented to a medical professional; initiating a signal for a plan of care to be initiated for the individual; preparing a treatment plan for the individual; automatically scheduling a caregiver to provide therapeutic treatment to the individual; modifying or generating a medical care computer program for treating the individual; and setting a schedule for future evaluations of the individual.

Embodiment 8: Computer storage media having computer-executable instructions embodied thereon that, when executed, facilitate a method for determining that an individual is at risk of onset of Stage 3 chronic kidney disease (CKD). The method comprises: obtaining a series of historical uric acid measurements taken for the individual over a period of time; determining a velocity of uric acid based on the series of historical uric acid measurements; obtaining current measurements for one or more physiological variables for the individual, the one or more physiological variables including uric acid level, estimated glomerular filtration rate (eGFR), and hemoglobin A1c (HbA1c); based on the velocity of uric acid and the current measurements for the one or more physiological variables, determining a forecast probability that the individual will progress to Stage 3 CKD within a future time interval; and evoking an action based on the forecast probability.

Embodiment 9: The computer storage media of embodiment 8, the forecast probability that the individual will progress to Stage 3 CKD within the future time interval is determined using a multi-variable logistic regression statistical model.

Embodiment 10: The computer storage media of any of embodiments 8-9, wherein prior to determining the forecast probability, the method further comprises: comparing the current measurement for the individual's uric acid level to an age-gender adjusted reference level of uric acid; comparing the current measurement of HbA1c to a reference level; and comparing the current measurement for eGFR with a reference minimum rate and a reference maximum rate.

Embodiment 11: The computer storage media of any of embodiments 8-10, wherein the velocity of uric acid that is determined is an annularized uric acid velocity.

Embodiment 12: The computer storage media of any of embodiments 8-11, wherein the future time interval is 36 months.

Embodiment 13: The computer storage media of any of embodiments 8-12, wherein the series of historical uric acid measurements comprises four measurements.

Embodiment 14: The computer storage media of any of embodiments 8-13, wherein the period of time over which the historical uric acid measurements are taken is between two years and five years.

Embodiment 15: The computer storage media of any of embodiments 8-14, wherein the method further comprises determining the forecast probability satisfies a threshold probability.

Embodiment 16: The computer storage media of any of embodiments 8-15, wherein the threshold probability is predetermined by at least one of a medical professional, medical care provider, or empirical evidence.

Embodiment 17: The computer storage media of any of embodiments 8-16, wherein the action evoked based on the forecast probability comprises at least one of: initiating a signal that causes an alert to be presented to a medical professional; initiating a signal for a plan of care to be initiated for the individual; preparing a treatment plan for the individual; automatically scheduling a caregiver to provide therapeutic treatment to the individual; modifying or generating a medical care computer program for treating the individual; and setting a schedule for future evaluations of the individual.

Embodiment 18: A computerized method for forecasting progression to Stage 3 chronic kidney disease (CKD) for an individual. The method comprises: generating a multi-variable logistic regression statistical model capable of calculating a probability of progression to Stage 3 CKD within a future time period of thirty-six months using a plurality of variables; receiving an input data set for the individual, the input data set comprising the individual's age, the individual's gender, a series of historical measurements of uric acid levels for the individual, a current uric acid level for the individual, an estimated glomerular filtration rate (eGFR) for the individual, and a current hemoglobin A1c (HbA1c) level for the individual; based on the multi-variable logistic regression statistical model and the input data set, determining a probability of the individual progressing to Stage 3 CKD within the future time period; and based on the probability of the individual progressing to Stage 3 CKD within the future time period, evoking an action corresponding to treatment for the individual.

Embodiment 19: The computerized method of embodiment 18, wherein the series of historical measurements of uric acid includes four uric acid measurements determined on distinct dates over a time period between two years and five years.

Embodiment 20: The computerized method of any of embodiments 18-19, wherein prior to determining the probability of the individual progressing the Stage 3 CKD within the future time interval, the method further comprises calculating a velocity of uric acid using the series of historical measurements of uric acid levels for the individual.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention.

It will be understood that certain features and subcombinations are of utility and may be employed without reference to other features and subcombinations and are contemplated within the scope of the claims. Not all steps listed in the various figures need be carried out in the specific order described. Accordingly, the scope of the invention is intended to be limited only by the following claims.

What is claimed is:

1. Computer storage media having computer-executable instructions embodied thereon that, when executed by at least one processor, cause the at least one processor to perform operations, the operations comprising:
   obtaining, at an electronic decision support tool embedded in an electronic health record (EHR) system, measurements of one or more physiological variables for an individual, the measurements including at least a longitudinal time series data of uric acid for the individual;
   appending, at the electronic decision support tool, information of the individual to the measurements;
   transforming the measurements of the one or more physiological variables to reflect non-linear relationships of the measurements according to gender, wherein a transformation process comprises of logistic transformation, min-max transformation, or thresholding according to each physiological variable of the one or more physiological variables;
   determining, at the electronic decision support tool, a uric acid quantile membership of the individual, wherein uric acid quantiles are determined by age groups for each gender;
   computing, at the electronic decision support tool, a uric acid velocity based on temporal analysis of the longitudinal time series data of uric acid measurements of the individual;
   determining statistically significant model variables for each gender based at least on the transformed measurements of the one or more physiological variables, the uric acid quantile membership, and the uric acid velocity;

generating a gender specific predictive model by using the statistically significant model variables, wherein the gender specific predictive model is configured to estimate coefficients corresponding to the statistically significant model variables and to predict progression of stage 3 chronic kidney disease (CKD);

computing, in real-time at the electronic decision support tool using the gender specific predictive model, automatically a forecast probability that the individual will progress to stage 3 CKD within a future time interval;

comparing, at the electronic decision support tool, the forecast probability to one or more threshold probabilities; and based on comparing the forecast probability to the one or more threshold probabilities, automatically generating and executing, by the electronic decision support tool, a health care software routine or software agent to at least initiate a signal that causes an alert to be presented to a medical professional that is indicative of risk of progression to stage 3 CKD of the individual and preparing a treatment plan, wherein the treatment plan for the individual includes administering a disease-modifying medication regimen for treating the individual, wherein the disease-modifying medication regimen comprises administering a diabetes therapy, a medication to reduce proteinuria, an aldosterone blockade, an angiotensin-converting-enzyme (ACE) inhibitor, an angiotensin receptor blocker (ARB), an erythropoietin therapy, an acidosis treatment, or a combination thereof.

2. The computer storage media of claim 1, wherein the forecast probability is generated using a multi-variable logistic statistical regression model.

3. The computer storage media of claim 1, wherein the future time interval is 36 months.

4. The computer storage media of claim 1, wherein the measurements of the one or more physiological variables further include a current uric acid level, an estimated glomerular filtration rate (eGFR), and a hemoglobin A1c (HbA1c) level.

5. The computer storage media of claim 1, wherein the health care software routine or software agent is automatically modified and executed upon determining the forecast probability satisfies the one or more threshold probabilities.

6. The computer storage media of claim 1, wherein the health care software routine or software agent being automatically modified and executed is further configured to perform at least one of:
   initiating a signal for a plan of care to be initiated for the individual;
   preparing a treatment plan for the individual;
   automatically scheduling a caregiver to provide therapeutic treatment to the individual; and
   setting a schedule for future evaluations of the individual.

7. A system comprising:
   one or more data processors; and
   a non-transitory computer readable storage medium containing instructions which, when executed on the one or more data processors, cause the one or more data processors to perform a set of operations including:
      obtaining, at an electronic decision support tool embedded in an electronic health record (EHR) system, measurements of one or more physiological variables for an individual, the measurements including at least a longitudinal time series data of uric acid for the individual;
      appending, at the electronic decision support tool, information of the individual to the measurements;
      transforming the measurements of the one or more physiological variables to reflect non-linear relationships of the measurements according to gender wherein a transformation process comprises of logistic transformation, min-max transformation, or thresholding according to each physiological variable of the one or more physiological variables;
      determining, at the electronic decision support tool, uric acid quantile membership of the individual, wherein uric acid quantiles are determined by age groups for each gender;
      computing, at the electronic decision support tool, a uric acid velocity based on temporal analysis of the longitudinal time series data of uric acid measurements of the individual;
      determining statistically significant model variables for each gender based at least on the transformed measurements of the one or more physiological variables, the uric acid quantile membership, and the uric acid velocity;
      generating a gender specific predictive model by using the statistically significant model variables, wherein the gender specific predictive model is configured to estimate coefficients corresponding to the statistically significant model variables and to predict progression of stage 3 chronic kidney disease (CKD);
      computing, in real-time at the electronic decision support tool using the gender specific predictive model, automatically a forecast probability that the individual will progress to stage 3 CKD within a future time interval;
      comparing, at the electronic decision support tool, the forecast probability to one or more threshold probabilities; and
      based on comparing the forecast probability to the one or more threshold probabilities, automatically generating and executing, by the electronic decision support tool, a health care software routine or software agent to at least initiate a signal that causes an alert to be presented to a medical professional that is indicative of risk of progression to stage 3 CKD of the individual and preparing a treatment plan, wherein the treatment plan for the individual includes administering a disease-modifying medication regimen for treating the individual, wherein the disease-modifying medication regimen comprises administering a diabetes therapy, a medication to reduce proteinuria, an aldosterone blockade, an angiotensin-converting-enzyme (ACE) inhibitor, an angiotensin receptor blocker (ARB), an erythropoietin therapy, an acidosis treatment, or a combination thereof.

8. The system of claim 7, the forecast probability that the individual will progress to stage 3 CKD within the future time interval is determined using a multi-variable logistic regression statistical model.

9. The system of claim 7, wherein prior to determining the forecast probability, the set of operations further includes:
   comparing a current measurement of uric acid level of the individual to an age-gender adjusted reference level of uric acid;
   comparing a current measurement of HbA1c to a reference level; and
   comparing a current measurement of eGFR with a reference minimum rate and a reference maximum rate.

10. The system of claim 7, wherein the uric acid velocity that is computed is an annualized uric acid velocity.

11. The system of claim 7, wherein the future time interval is 36 months.

12. The system of claim 7, wherein the longitudinal time series data of uric acid measurements comprises four measurements.

13. The system of claim 7, wherein a period of time over which the longitudinal time series data of uric acid measurements is taken between two years and five years.

14. The system of claim 7, wherein the set of operations further includes:
determining the forecast probability satisfies a threshold probability of the one or more threshold probabilities.

15. The system of claim 7, wherein the one or more threshold probabilities are predetermined by at least one of a medical professional, a medical care provider, or an empirical evidence.

16. The system of claim 7, wherein the health care software routine or software agent being automatically modified and executed is further configured to perform at least one of:
initiating a signal for a plan of care to be initiated for the individual;
preparing a treatment plan for the individual;
automatically scheduling a caregiver to provide therapeutic treatment to the individual; and
setting a schedule for future evaluations of the individual.

17. A computerized method comprising:
obtaining, at an electronic decision support tool embedded in an electronic health record (EHR) system, measurements of one or more physiological variables for an individual, the measurements including at least a longitudinal time series data of uric acid for the individual
appending, at the electronic decision support tool, information of the individual to the measurements;
transforming the measurements of the one or more physiological variables to reflect non-linear relationships of the measurements according to gender, wherein a transformation process comprises of logistic transformation, min-max transformation, or thresholding according to each physiological variable of the one or more physiological variables;
determining, at the electronic decision support tool, a uric acid quantile membership of the individual, wherein uric acid quantiles are determined by age groups for each gender;
computing, at the electronic decision support tool, a uric acid velocity based on temporal analysis of the longitudinal time series data of uric acid measurements of the individual;
determining statistically significant model variables for each gender based at least on the transformed measurements of the one or more physiological variables, the uric acid quantile membership, and the uric acid velocity;
generating a gender specific predictive model by using the statistically significant model variables, wherein the gender specific predictive model is configured to estimate coefficients corresponding to the statistically significant model variables and to predict progression of stage 3 chronic kidney disease (CKD);
computing, in real-time at the electronic decision support tool using the gender specific predictive model, automatically a forecast probability that the individual will progress to stage 3 CKD within a future time interval;
comparing, at the electronic decision support tool, the forecast probability to one or more threshold probabilities; and
based on comparing the forecast probability to the one or more threshold probabilities, automatically generating and executing, by the electronic decision support tool, a health care software routine or software agent to at least initiate a signal that causes an alert to be presented to a medical professional that is indicative of risk of progression to stage 3 CKD of the individual and preparing a treatment plan, wherein the treatment plan for the individual includes administering a disease-modifying medication regimen for treating the individual, wherein the disease-modifying medication regimen comprises administering a diabetes therapy, a medication to reduce proteinuria, an aldosterone blockade, an angiotensin-converting-enzyme (ACE) inhibitor, an angiotensin receptor blocker (ARB), an erythropoietin therapy, an acidosis treatment, or a combination thereof.

18. The computerized method of claim 17, wherein the longitudinal time series data of uric acid includes four uric acid measurements determined on distinct dates over a time period between two years and five years.

19. The computerized method of claim 17, wherein the health care software routine or software agent is further configured to:
prepare a treatment plan for the individual.

20. The computerized method of claim 17, wherein the health care software routine or software agent is further configured to:
automatically schedule a caregiver to provide therapeutic treatment to the individual.

* * * * *